US005824656A

United States Patent [19]
Profous-Juchelka et al.

[11] Patent Number: 5,824,656
[45] Date of Patent: Oct. 20, 1998

[54] **RECOMBINANT AND NATIVE GROUP B *EIMERIA TENELLA* IMMUNOGENS USEFUL AS COCCIDIOSIS VACCINES**

[75] Inventors: Helen Profous-Juchelka, Staten Island, N.Y.; Mervyn J. Turner, Westfield; Paul A. Liberator, Holmdel, both of N.J.

[73] Assignee: Merck & Co., Inc., Rahway, N.J.

[21] Appl. No.: 458,590

[22] Filed: Jun. 2, 1995

Related U.S. Application Data

[63] Continuation-in-part of Ser. No. 87,914, Jul. 6, 1993, abandoned, which is a continuation of Ser. No. 695,485, May 3, 1991, abandoned, which is a continuation of Ser. No. 588,510, Sep. 21, 1990, abandoned, which is a continuation of Ser. No. 286,936, Dec. 22, 1988, abandoned, which is a continuation of Ser. No. 145,802, Jan. 15, 1988, abandoned.

[51] Int. Cl.$^6$ .......................... A61K 48/00; C07H 21/04
[52] U.S. Cl. ............................................. 514/44; 536/23.5
[58] Field of Search ........................... 424/191.1; 514/44; 536/23.5

[56] References Cited

U.S. PATENT DOCUMENTS

| | | |
|---|---|---|
| 4,639,372 | 1/1987 | Murray et al. . |
| 4,650,676 | 3/1987 | Schenkel et al. . |
| 4,710,377 | 12/1987 | Schenkel et al. . |
| 5,187,080 | 2/1993 | Andrews et al. . |
| 5,279,960 | 1/1994 | Andeson et al. . |

FOREIGN PATENT DOCUMENTS

| | | |
|---|---|---|
| 135073 | 7/1984 | European Pat. Off. . |
| 167443 | 6/1985 | European Pat. Off. . |
| 164176 | 12/1985 | European Pat. Off. . |
| 231537 | 11/1986 | European Pat. Off. . |
| 241139 | 10/1987 | European Pat. Off. . |
| 344808 | 2/1989 | European Pat. Off. . |
| WO 86/00528 | 1/1986 | WIPO . |
| WO 88/06629 | 3/1988 | WIPO . |
| WO 92/04460 | 9/1991 | WIPO . |
| WO 92/04461 | 9/1991 | WIPO . |

OTHER PUBLICATIONS

Aviv and Leder, Purification of Biologically Active Globin Messenger RNA by Chromatography on Oligothymidylic acid–Cellulose, Proc. Natl. Acad. Sci. USA 69: 1408–1412 (1972).
Bethell et al., A Novel Method of Activation of Cross–Linked Agaroses with 1,1'–Carbonyldiimidazole Which gives a Matrix for Affinity Chromatography Devoid of Additional Charged Groups, J. Biol. Chem. 254: 2572–2574 (1979).
Bhanushali and Long, Role of Sporozite Induced Responses In Protection Against *Eimeria Tenella*: In Vivo & In Vitro Studies, In "Research In Avian Coccidiosis," McDougald et al. etd, Proceedings of Georgia Coccidiosis Conf., pp. 526–534 (1985).
Chirgwin et al., Isolation of Biologically Active Ribonucleic Acid from Sources Enriched in Ribonuclease, Biochem. 18: 5294–5299 (1979).
Clarke et al., Isolation of λamp3 genomic recombinants coding for antigens of *Eimeria tenella*. Mol. and Biochem. Parasit, 22: 79–87 (1987).
Corthier et al., Improved Method for IgG Purification from Various Animal Species by Ion Exchange Chromatography, J. Immunol. Meth. 66: 75–79 (1984).
Crane et al., Passive Protection of Chickens agains *Eimeria tenella* Infection by Monoclonal Antibody, Infect. Immun. 56: 972–976 (1988).
Davis et al. Basic Methods In Molecular Biology, Elsievier, New York New York, p. 30 (1986).
S. A. Edgar, Effect of Temperature on the Sporulation of Oocysts of The Protozoan, *Emeria tenella*, Trans. Am. Micr. Soc. 62: 237–242 (1954).
Gubler and Hoffman, A simple and very efficient method for generating cDNA libraries, Gene 25: 263–269 (1983).
Hall et al., Major surface antigen gene of a human malaria parasite cloned and expressed in bacteria, Nature 311: 379–382 (1984).
Hattori and Sakaki. Dideoxy Sequencing Method Using Denatured Plasmid Templates Anal. Biochem. 152: 232–238 (1986).
Huynh et al., Constructing and Screening cDNA Libraries in λgt10 and λgt11 In "DNA cloning: A practical Approach," vol. 1, Glover Ed., IRL Press, Oxford, pp. 49–78 (1985).
Ish–Horowitz & Burke, Rapid and efficient cosmid cloning, Nucleic Acids Research 9: 2989–2998 (1981).
A. R. B. Jackson, The Isolation of viable coccidial sporozoites, Parasitol. 54: 87–93 (1964).
Kohler and Milstein, Continuous cultures of fused cells secreting antibody of predefined specificity, Nature 256: 495–497 (1975).
U.K. Laemmli, Cleavageof Structural Proteins during the Assembly of the Head of Bacteriophage T4, Nature 227: 680–684 (1970).
Long et al., Immunization against coccidiosis in chickens: Tests under simulated field conditions, Biol. Abst. 75, No. 3, p. 1904, Ref. 18594 (1982).
Lowry et al., Protein Measurement With the Folin Phenol Reagent, J. Biol. Chem. 193: 265–275 (1951).
I. MacPherson, Soft Agar Techniques, in "Tissue Culture Methods and Applications," Academic Press, pp. 276–277 (1973).

(List continued on next page.)

*Primary Examiner*—Lila Feisee
*Assistant Examiner*—Geetha P. Bansal
*Attorney, Agent, or Firm*—Michael D. Yablonsky; Jack L. Tribble

[57] ABSTRACT

Genes coding for novel Group B *Eimeria tenella* protein immunogens have been isolated and inserted into a novel expression vector which in turn has been used to transform appropriate hosts. The transformed host cells produce recombinant Group B *E. tenella* proteins which are capable of inducing immunity in chickens to coccidiosis.

4 Claims, 8 Drawing Sheets

OTHER PUBLICATIONS

Lehrach et al.. Electrophoresis of RNA through Gels Containing Formaldehyde, in Molecular Cloning, A Laboratory Manual Maniatis et al. (Eds). Cold Spring Harbor Lab. 202–203 and 468–469 (1982).

Mason and Williams, Hybridisation in the Analysis of Recombinant DNA, In Nucleic Acid Hybridization: A Practical Approach, Hames and Higgens, Eds., IRL Press pp. 113–137 (1985).

Matsumura et al.. Overexpression and Sequence of the *Escherichia coli* cheY Gene and Biochemical Activities of the CheY Protein, J. Bacteriol. 160: 36–41 (1984).

Maxam and Gilbert, Sequencing End–Labeled DNA with Base–Specific, Chemical Cleavages, Methods in Enzymology 65 (part 1): 499–559 (1980).

McDonald et al., *Eimeria tenella*: immunogenicity of the first generation of schizogony, Parasitol. 93: 1–7 (1986).

J. Messing, New M13 Vectors for Cloning, Methods in Enzymology 101: 20–78 (1983).

PH. O'Farrell, High Resolution Two–Dimensional Electrophoresis of Proteins, J. Biol. Chem. 250: 4007–4021 (1975).

Okayama and Berg, High–Efficiency Cloning of Full––Length cDNA, Mol. Cell Biol. 2: 161–170 (1982).

Old and Primose, Principles of Gene Manipulation: University of Calif. Press, p. 20 (1981).

W. H. Patton, *Eimeria tenella*: Cultivation of the Asexual Stages In Cultured Animal Cells, Science 150: 767–769 (1965).

Patton et al., The Use of Sodium Taurodeoxycholate for Excystation of *Eimeria Tenella* Sporozoites, J. Parasitol. 65:526–530 (1979).

Rose and Hesketh, Immunity to coccidiosis: states of the life–cycle of *Eimeria maxima* which induce, and are affected by, the response of the host, Parastiol, 73: 25–37 (1976).

Santoro et al., Structural Simularities amond the Protective Antigens of Sporozoites from Different Species of Malaria Parasites, J. Biol: Chem. 258: 3341–3345 (1983).

Schmatz et al., Purification of *Eimeria Sporozoites* by DE–52 Anion Exchange Chromatography, J. Protozool. 31: 181–183 (1984).

Schneider et al., A One–Step Purification of Membrane Proteins Using a High Efficiency Immunomatrix, J. Biol. Chem. 257: 10766–10769 (1982).

Smithies et al., Cloning Human Fetal γ Globin and Mouse α–Type Globin DNA: Characterization and Partial Sequencing, Science 202: 1285–1289 (1978).

Tabor and Richardson, DNA sequence analysis with a modified bacteriophage T/ DNA polymerase, Proc. Natl. Acad. Sci. USA 84: 4767–4771 (1987).

Taylor et al., Immunoprecipitation of Surface Antigen Precursors From Schistosoma Mansoni Messinger RNA In Vitro Translation Products, Mol. Biochem. Parasitol. 10: 305–318 (1983).

Temeles et al., Yeast and mammalian ras proteins have conserved biochemical properties, Nature 313: 700–703 (1985).

Towbin et al., Electrophoretic transfer of proteins from polyacrylamide gels to nitrocellulose sheets: Procedure and some applications, Proc. Natl. Acad. Sci. USA 76: 4350–4354 (1979).

D.M. Weir (Ed.) Handbook of Experimental Immunology, Blackwell Scientific Publ. London, pp. A3–11—A3–15 (1978).

M. H. Wisher, Identification of the sporozoite antigens of *Eimeria tenella*, Mol. Biochem. Parasitol. 21: 7–15 (1986).

Yanisch–Perron et al., Improved M13 phage cloning vectors and host strains nucleotide sequences of the M13mp18 and pUC19 vectors, Gene 33: 103–109 (1985).

(out of order) S. James, Isolation of second–generation schizonts of avian coccidia and their use in biochemical investigations, Parasitol. 80: 301–312 (1980).

(out of order) Johnson and Reid, Anticoccidial Drugs: Lesion Scoring Techniques in Battery and Floor–Pen Experiments with Chickens, Expt. Parasitol. 28: 30–36 (1970).

Clarke et al., Isolation of λamp3 genomic recombinants coding for antigens of *eimeria tenella*, Chem. Abs. 106: p. 189.

H. Profous–Juchella et al., Identification and characterization of cDNA Clones encoding antigens of *Eimeria tenella*, Chem. Abs. 109: 374.

Augustine, et al., "Use of Monoclonal Ab to Study . . . ", Proc. of Helminth. Soc. Wash., vol. 54, No. 2, pp. 207–211 (1987).

Davis et al, DNA Based Immunization Induces Continous Secretion of Hepatitis B Surface Antigen and High Levels of Circulating Antibody Human Molecules Genetics, 1993 vol. 2 No. 11 1847–1851.

Montgomery et al, Heterologous and Homologous Protection Against Influenza A by DNA Vaccination: Optimization of DNA Vectors, DNA & Cell Biology vol. 12, No. 9, 1993 pp. 777–783.

Fynan et al, Use of DNA encoding Influenza Hemaglutinin as an Avian Influenza Vaccine DNA and Cell Biology vol. 12, No. 9 1993 pp. 785–789.

RECOMBINANT AND NATIVE GROUP B EIMERIA TENELLA IMMUNOGENS USEFUL AS COCCIDIOSIS VACCINES

RELATED U.S. APPLICATION DATA

This is a continuation-in-part of Ser. No. 08/087,914, filed Jul. 6, 1993, now abandoned, which is a continuation of Ser. No. 07/695,485, filed May 3, 1991, now abandoned, which is a continuation of Ser. No. 07/588,510, filed Sep. 21, 1990, now abandoned, which is a continuation of Ser. No. 07/286,936, filed Dec. 22, 1988, now abandoned, which is a continuation-in-part of Ser. No. 07/145,802, Jan. 15, 1988, now abandoned.

BACKGROUND OF THE INVENTION

Figure 1:
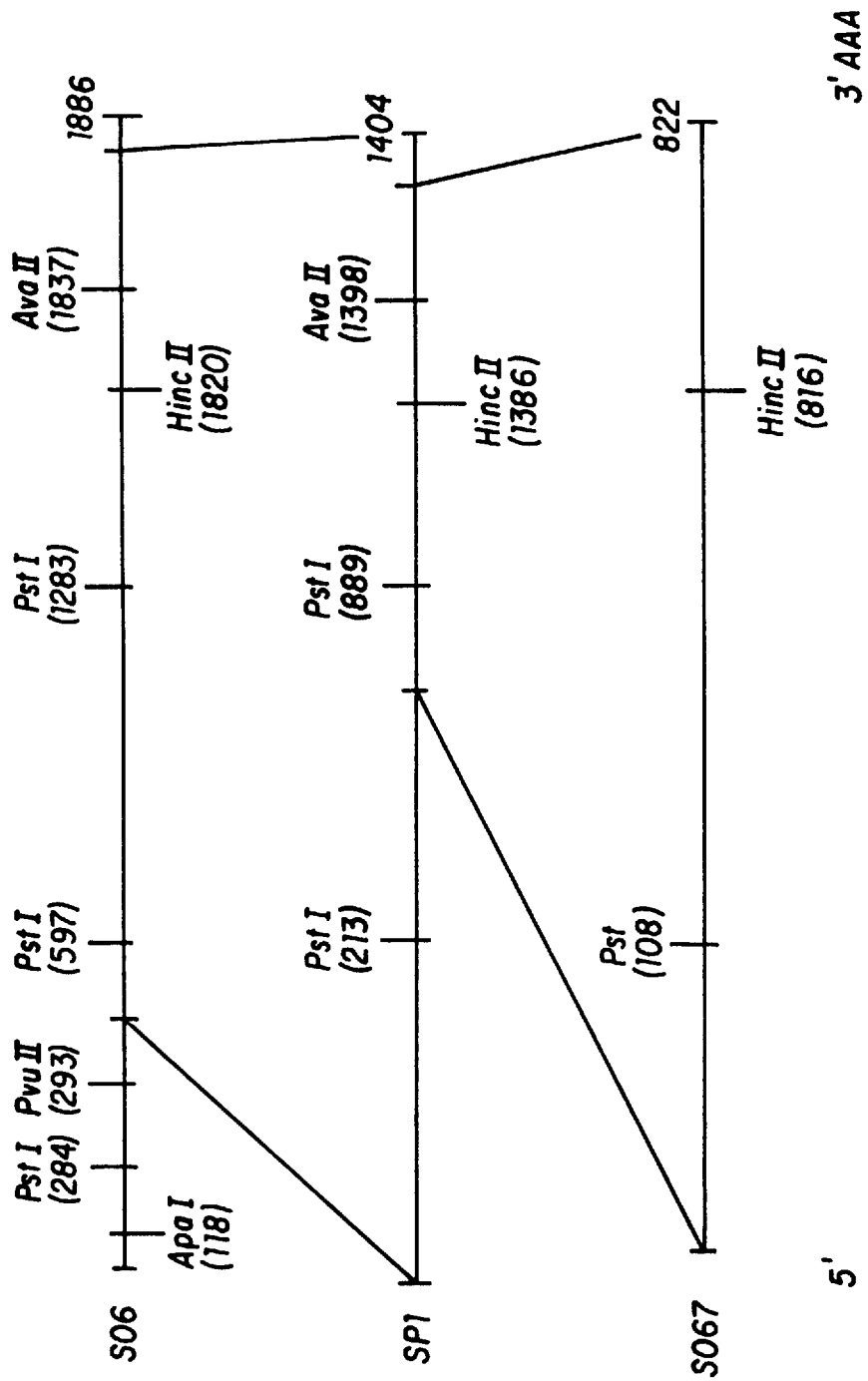
FIG. 1 is a restriction map of group A clones. The SO6 gene is about 1886 nucleotides (nt) in length with restriction sites at the following base locations: 118 (ApaI), 284 (PstI), 293 (PvuII), 597 (PstI), 1283 (PstI), 1820 (HincII) and 1837 (AvaII). The SPI gene is about 1404 nt with restriction sites at the following base locations: 213 (PstI), 889 (PstI), 1386 (HincII) and 1398 (AvaII). The SO67 gene is 822 nt in length with restriction sites at the following base locations: 108 (PstI), and 816 (HincII).
Figure 2:
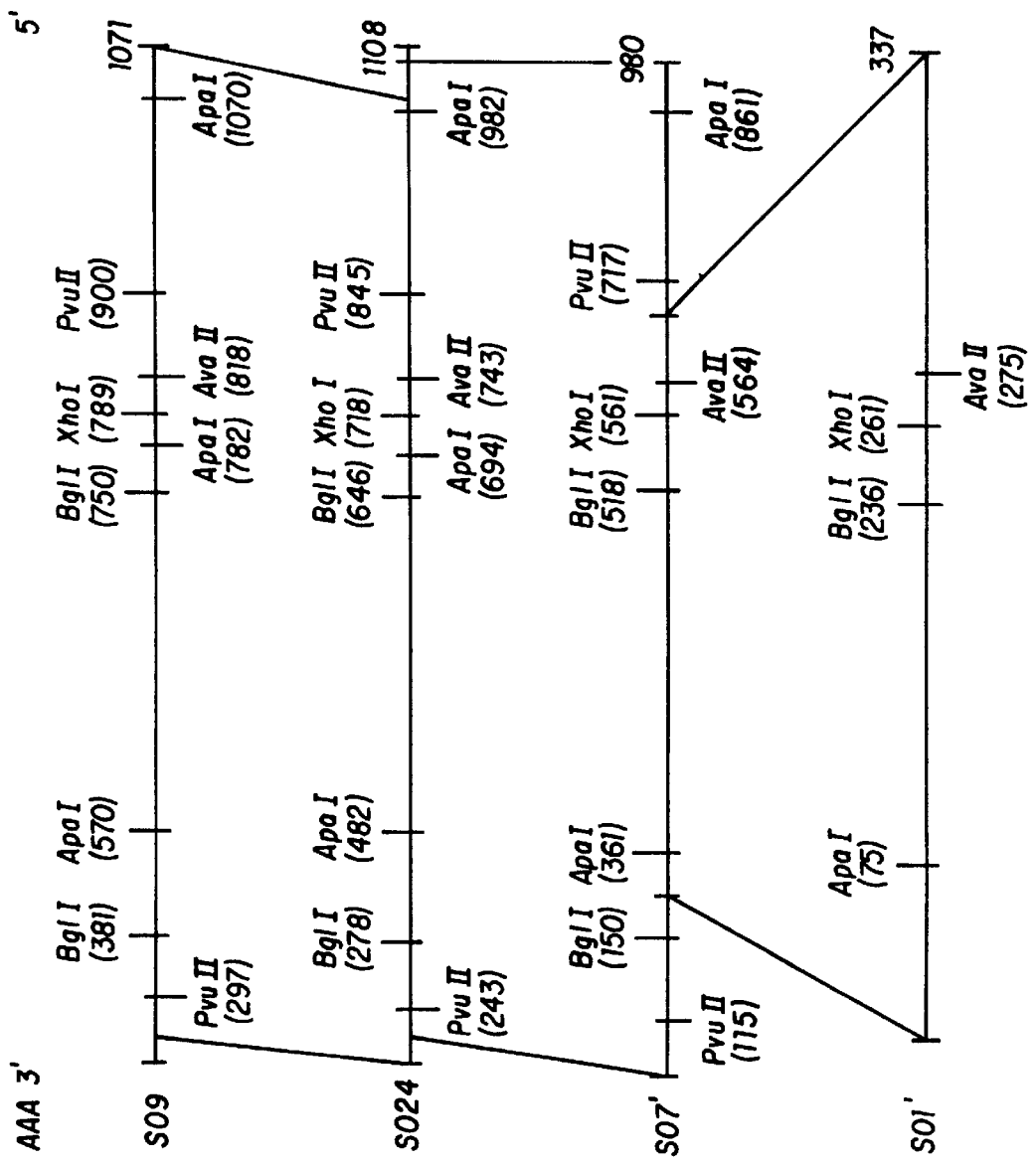
FIG. 2 is a restriction map of group B clones. The SO9 gene is about 1071 nt in length with restriction sites at the following base locations: 297 (PuvII), 381 (BglI), 570 (ApaI), 750 (BglI), 789 (XhoI) and 900 (PvuII). The SO24 gene is about 1108 nt in length with restriction sites at the following base locations: 243 (PvuII), 278 (BglI), 482 (ApaI), 646 (BglI), 694 (ApaI), 718 (XhoI), 743 (AvaII), 845 (PvuII) and 982 (ApaI). The SO7 gene is about 980 nt in length with restriction sites at the following base locations: 115 (PvuII), 150 (BglI), 361 (ApaI), 518 (BglI), 561 (XhoI), 564 (AvaII), 717 (PvuII) and 861 (ApaI). The SO7' gene is identical to the SO7 gene. The SO1 gene is about 337 nt in length with restriction sites at the following base locations: 75 (ApaI), 236 (BglI), 261 (XhoI) and 275 (AvaII).
Figure 3:
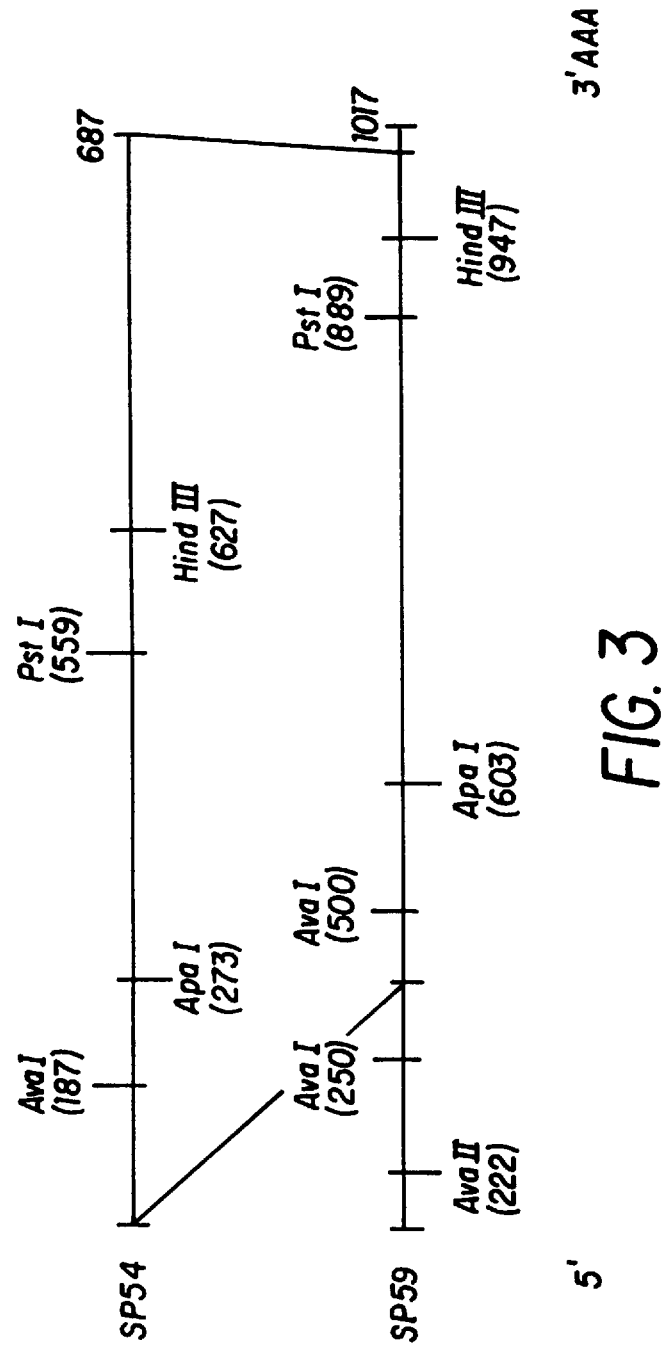
FIG. 3 is a restriction map of group C clones. The SP54 gene is about 687 nt in length with restriction sites at the following base locations: 187 (AvaI), 273 (ApaI), 559 (PstI) and 627 (HindIII). The SP59 gene is about 1017 nt in length with restriction sites at the following base locations: 222 (AvaII), 250 (AvaI), 500 (AvaI), 603 (ApaI), 682 (ApaI), 889 (PstI) and 947 (HindIII).
Figure 4:
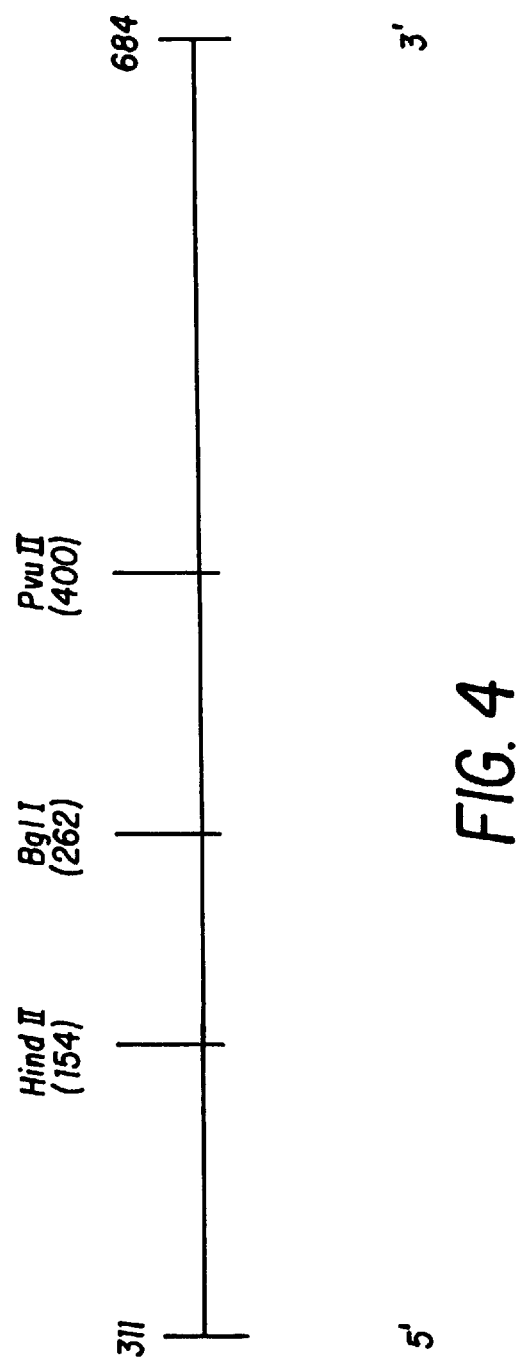
FIG. 4 is a restriction map of group H clones. The SO311 gene is about 684 nt in length with restriction sites at the following base locations: 154 (HincII), 262 (BglI) and 400 (PvuII). The SO227 gene is 631 nt in length with restriction sites at the following base locations: 257 (HincII), 369 (BglI) and 537 (PvuII). The SO231 gene is 632 nt in length with restriction sites at the following base locations: 255 (HincII), 382 (BglI) and 514 (PvuII).
Figure 5:
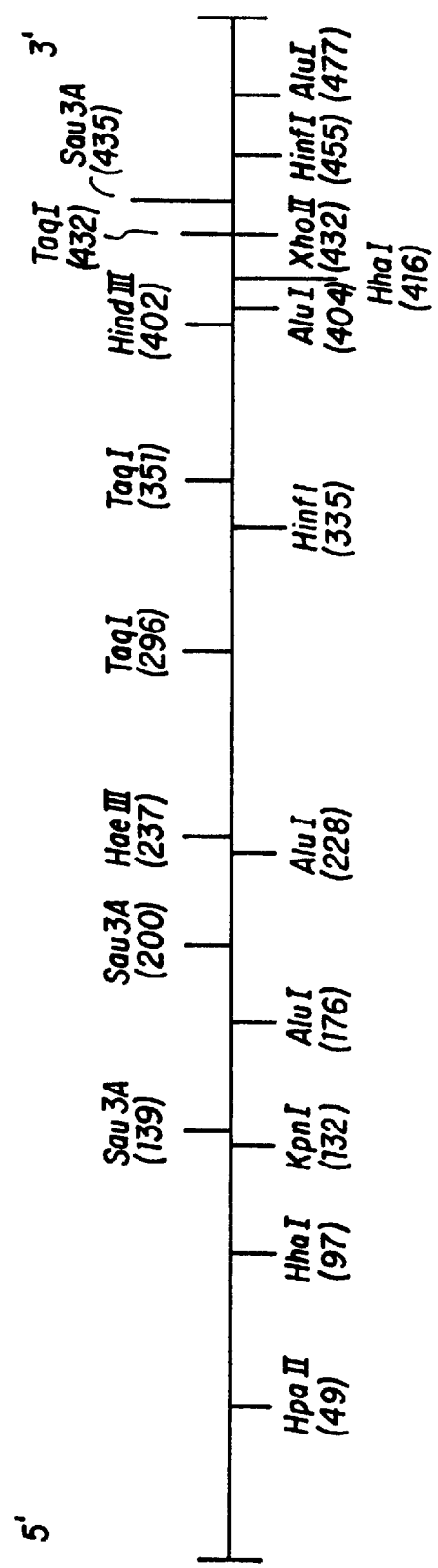
FIG. 5 is a restriction map of group F clones. The SO216 gene is about 487 nt in length with restriction sites at the following base locations: 49 (HpaII), 97 (HhaI), 132 (KpnI), 139 (Sau3A), 176 (AluI), 200 (Sau3A), 228 (AluI), 237 (HaeIII), 296 (TaqI), 335 (HinfI), 341 (TaqI), 402 (HindIII), 404 (AluI), 415 (HhaI), 432 (TaqI), 435 (XhoII), 435 (Sau3A), 455 (HinfI) and 477 (AluI). The first eight nts and the last eight nts represent the linker nts and are not part of the *E. tenella* Group F gene.

Coccidiosis is a disease caused by infection with one or more of the many species of coccidia. Coccidia are intracellular parasites which can infect a wide range of hosts and may result in severe economic loss to the sheep, goat, cattle, swine and poultry industry. Indeed, coccidiosis resulting from infection with Eimeria species has caused economically devastating losses to the poultry industry. Among domesticated birds, chicken production is the most susceptible to the economic losses from coccidiosis, although losses also occur with turkeys, geese, ducks, and guinea fowl. Coccidiosis also produces serious losses in pheasants and quail raised in captivity. Coccidiosis may be acute and characterized by devastating flock mortality or the disease may be chronic and characterized by lack of weight gain.

Poultry are infected by coccidia following ingestion of the vegetative stage of the parasite, the sporulated oocyst. The infective stage, the sporozoite, is released in the intestine where it rapidly invades epithelial cells subsequently undergoing several generations of rapid intracellular asexual multiplication (schizogony) before entering the stage of sexual differentiation and mating (gametogony) leading to the formnation of immature oocysts. Immature oocysts are shed in droppings; the immature oocysts then undergo an extracellular sporulation process (sporogony) resulting in the generation of mature oocysts. Low level infection with any of the Eimeria species (spp.), *E. acervulina, E. mivati, E. mitis, E. praecox, E. hagani, E. necatrix, E. maximal, E. brunetti* and *E. tenella* results in a protective immunity to reinfection. There may be as many as twelve distinct cell types involved in the development of the parasite, each morphologically and antigenically different. At least three of these cell types have been shown to induce a protective immune response in the host. Both the sporozoite as well as the first and second generation schizont appear to contain antigens which elicit an immunizing effect in chickens.

Unlike the sporozoite surface of other parasites such as *Plasmodium falciparum* which is composed of a single dominant antigen, the sporozoite surface of the Eimeria spp. generally and, in particular, *E. tenella* sporozoite surface, is antigenically complex. Because the sporozoite stage cannot be cultivated in vitro and large amounts of sporozoite material would be necessary for conventional biochemical analysis and for subunit vaccine evaluation, the purification of these antigens has posed a problem.

Schenkel, et al.(European Patent Application Number 135,712) showed that solubilized *E. tenella* sporozoite proteins, identified by monoclonal antibodies prepared against intact *E. tenella* sporozoites protected chickens against challenge with infective oocysts. Similar results were obtained with *E. tenella* merozoites prepared by the same techniques. Immunogenic polypeptides have been isolated from *E. tenella* sporozoites. There was no indication, however, that any individual polypeptide would protect chickens against *E. tenella* challenge.

Recombinant DNA technology has allowed for the identification of immunogenic Eimeria polypeptides and for the production of the polypeptides in sufficient quantities for vaccine development. Newman, et al. (European Patent Application 164,176) describe the isolation of a 25,000 dalton polypeptide from *E. tenella* the polypeptide is made up of two subunits of 17,000 and 8,000 daltons respectively. The 25,000 dalton polypeptide was produced by recombinant DNA technology utilizing a genomic DNA clone and was shown to protect chickens against coccidiosis caused by *E. tenella*. Another immunogenic *E. tenella* polypeptide was disclosed by Anderson and McCandliss (WO 86/00528). This peptide was sequenced, is composed of 280 amino acids, has been produced by recombinant DNA technology utilizing both an oocyst genomic DNA clone and a clone isolated from total oocyst mRNA, and protects chickens against coccidiosis. Clark, et al.(Mol. Biochem. Parasit. 22:79–87, 1987) disclosed the construction of genomic DNA expression libraries from *E. tenella* in *Escherichia coli*. Clones expressing *E. tenella* immunogens were detected, none of the peptides were tested for immunogenic activity. *E. tenella* sporozoite surface membranes have been labeled by various techniques to characterize potential surface immunogens by Wisher (Mol. Biochem. Parasit, 21:7–15, 1986). The major surface polypeptides which reacted with anti-*E. tenella* antibody were in the following ranges: 113–96 kD, 73–67 kD, 54–42 kD, 37–32 kD, and 18–14 kD.

The present invention relates to coccidiosis vaccines based on either native or recombinant-derived purified protein immunogens and microheterogeneous or subunit immunogen forms of the protein associated with sporulated oocysts, sporozoites, schizonts and merozoites of *E. tenella*. Genes coding for novel Group B *E. tenella* protein immunogens have been isolated, inserted into a novel expression vector, and used to transform appropriate hosts. The transformed host cells produce recombinant Group B *E. tenella* proteins which are capable of inducing immunity in chickens to coccidiosis. Antibody prepared against the recombinant protein immunogens is used to isolate and identify the native protein from disrupted *E. tenella* sporulated oocysts. The present invention to provide novel proteins of *E. tenella* which can be used to immunize chickens against coccidiosis. The present invention also provides immunogenic proteins specifically associated with sporulated oocysts and sporozoites. The present invention also provides the deduced amino acid sequence of the immunogenic proteins. The present invention further provides genes coding for the specific protein immunogens and incorporates the genes into appropriate expression vectors. Another aspect of the invention is to transform an appropriate host with each of the recombinant vectors, to induce expression of the specific coccidial genes and to isolate the pure immunogens. Another feature is to produce a novel expression vector for the expression of the specific coccidial proteins. A further aspect is monospecific antibodies reactive against the immunogenic proteins.

SUMMARY OF THE INVENTION

Genes coding for novel Group B *E. tenella* protein immunogens have been isolated, inserted into a novel expression vector, and used to transform appropriate hosts. The transformed host cells produce recombinant Group B *E. tenella* proteins which are capable of inducing immunity in chickens to coccidiosis. Antibody prepared against the recombinant protein immunogens is used to isolate and identify the native protein from disrupted *E. tenella* sporulated oocysts. It is accordingly, an object of the present invention to provide novel proteins of *E. tenella* which can be used to immunize chickens against coccidiosis. Another object is to provide immunogenic proteins specifically associated with sporulated oocysts and sporozoites. A further object is to provide the deduced amino acid sequence of the immunogenic proteins. Another object is to isolate genes coding for the specific protein immunogens and to incorporate the genes into appropriate expression vectors. A further object is to transform an appropriate host with each of the recombinant vectors, to induce expression of the specific coccidial genes and to isolate the pure immunogens. Another object is to produce a novel expression vector for the expression of the specific coccidial proteins. A further object is to produce monospecific antibodies reactive against the immunogenic proteins.

DETAILED DESCRIPTION OF THE INVENTION

The present invention relates to coccidiosis vaccines based on either native or recombinant-derived purified protein immunogens and microheterogeneous or subunit immunogen forms of the protein associated with sporulated oocysts, sporozoites, schizonts and merozoites of *E. tenella*.

The invention further relates to isolation and purification of the genetic information responsible for individual protein and the methods of expressing the corresponding immunogenic proteins.

The present invention relates to coccidiosis vaccines based on either native or recombinant-derived purified protein immunogens and microheterogeneous or subunit immunogen forms of the protein associated with sporulated oocysts, sporozoites, schizonts and merozoites of *E. tenella*. Genes coding for novel Group B *E. tenella* protein immunogens have been isolated, inserted into a novel expression vector, and used to transform appropriate hosts. The transformed host cells produce recombinant Group B *E. tenella* proteins which are capable of inducing immunity in chickens to coccidiosis. Antibody prepared against the recombinant protein immunogens is used to isolate and identify the native protein from disrupted *E. tenella* sporulated oocysts. The present invention to provide novel proteins of *E. tenella* which can be used to immunize chickens against coccidiosis. The present invention also provides immunogenic proteins specifically associated with sporulated oocysts and sporozoites. The present invention also provides the deduced amino acid sequence of the immunogenic proteins. The present invention further provides genes coding for the specific protein immunogens and incorporates the genes into appropriate expression vectors. Another aspect of the invention is to transform an appropriate host with each of the recombinant vectors, to induce expression of the specific coccidial genes and to isolate the pure immunogens. Another feature is to produce a novel expression vector for the expression of the specific coccidial proteins. A further aspect is monospecific antibodies reactive against the immunogenic proteins.

Polypeptide or protein as used herein refers to a linear polymer of amino acids bound together with amide linkages. The sequence of amino acids in the chain is of critical importance in the biological functioning of the protein or polypeptide. Polypeptide and protein are used interchangeably herein. Native protein as used herein refers to the full length protein produced by the appropriate Eimeria gene in the parasite. Recombinant-derived refers to the isolation of a gene for a desired protein and the use of that purified gene to construct a bacterium which will overproduce the desired protein. Subunit immunogen forms is defined as a portion of an immunogenic protein or polypeptide which has fewer amino acids than the native immunogenic moiety but contains the immunogenic site or sites of the immunogen. Microheterogeneous forms as used herein refers to a single gene product, that is a protein produced from a single gene unit of DNA, which is structurally modified following translation. These structural modifications, however, do not result in any significant alterations of the immunogenic activity of the protein. The modifications may take place either in vivo, in the parasite, or during the isolation and purification process. In vivo modification may result in, but is not limited to, acetylation at the N-terminus, proteolysis, glycosylation or phosphorylation. Proteolysis may include exoproteolysis wherein one or more tproduce micro acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which may result in the production of microheterogeneous forms. The most common modification occurring during purification is proteolysis which is generally held to a minimum by the use of protease inhibitors.

Poultry is defined herein as domesticated birds that serve as a source of eggs or meat and that include among commercially important kinds chickens, turkeys, ducks, geese, guinea fowl, pheasants, pigeons and peafowl.

A subunit vaccine as used herein is defined as a peptide, polypeptide or protein which is either isolated from one or more of the life stages of any species of Eimeria or is produced by recombinant DNA technology and which either individually or combined with other such peptides, polypeptides or proteins induces a protective immunity in poultry following vaccination. The recombinant antigens or immunogens will be similar to the peptides, polypeptides or proteins isolated from one or more life stages of Eimeria.

Immunogen is defined as a substance that when introduced into the body stimulates an immune response which is protective in nature, such as the use of a vaccine to produce immunity against a microorganism. Immunity is defined as decreased susceptibility to the invasive or pathogenic effects of foreign organisms or the toxic effects of products of foreign organisms. The protective immunity may be either humoral or cell-mediated immunity. Humoral immunity is defined as specific immunity mediated by antibodies which are present in the plasma, lymph and tissue fluids of the body, and which may become attached to cells. Cell-mediated immunity is defined as specific immunity mediated by T lymphocytes. Immunogen as used herein refers to molecules or macromolecules which when introduced into an animal body stimulates a humoral and/or a cellular immune response which is functional in nature, that is an immunity which protects the animal from a specific infection. In the instant case an immunogen will produce an immune response, either humoral, cellular or both which will protect poultry against infection with Eimeria species which cause coccidiosis. Antigen is used herein to define a substance capable of specifically combining with specific antibody. Antigen as used herein is defined as any substance that can combine with an antibody. Immunogens as described above are considered antigens when used to characterize the specific antibody.

Monospecific antibody as used herein is defined as a single antibody species or multiple antibody species with homogenous binding characteristics for the relevant antigen. Homogenous binding as used herein refers to the ability of the antibody species to bind to a specific antigen or epitope, such as those associated with the specific native or recombinant E. tenella group immunogens.

Recombinant DNA technology is defined herein as technology which allows segments of genetic information, DNA, from different cells, usually from different organisms, to be joined end-to-end outside the organisms from which the DNA was obtained and to incorporate this hybrid DNA into a cell that will allow the production of the protein for which the original DNA encodes.

Since none of the coccidial polypeptides, described above, which confer immunity, are capable of being purified to homogeneity by known separation or purification methods it has been impossible to characterize the amino acid composition of the individual polypeptides. Consequently, the antibodies directed against the various Eimeria antigens are used to identify by immunological methods, protective coccidial immunogenic polypeptides produced by recombinant DNA technology. Genetic information, DNA or mRNA, is isolated from sporulating oocysts or sporozoites, incorporated into an appropriate cloning vector, transduced into an appropriate host cell and products of the host cell screened for the production of polypeptides which bind to the anti-E. tenella antibodies. The identified genes expressing the immunoreactive polypeptides are incorporated into an appropriate expression vector and expressed in an appropriate host cell system.

Cloning vector as used herein is defined as a DNA sequence which allows the incorporation of specific experimental foreign DNA, with the combined DNA being introduced into a host cell that can exist in a stable manner and express the protein dictated by the experimental DNA. The foreign DNA combined with the vector DNA constitutes a recombinant DNA molecule which is derived from recombinant technology. Cloning vectors may include plasmids, bacteriophage, viruses and cosmids. It is to be understood that any cloning vector may be used to clone the novel Eimeria immunogen DNA sequences, with the lambda gt11 being preferred. Host cells for cloning, DNA processing and initial expression generally include bacteria. The preferred cloning host is Escherichia coli. Expression vectors are defined herein as DNA sequences that are required for the transcription of cloned copies of genes and the translation of their mRNAs in an appropriate host. Such vectors can be used to express either procaryotic or eucaryotic genes in a variety of hosts such as bacteria, blue-green algae, yeast cells, insect cells and animal cells. The immunogens may also be expressed in a number of virus systems. Specifically designed vectors allow the shuttling of DNA between bacteria-yeast or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The unique immunogenic proteins of the present invention may exist as, but are not limited to, the complete proteins specified by the defined gene in Eimeria, native protein or as any fragment or subunit thereof, or as hybrids of the complete protein or its fragments or subunits. The complete protein refers to the full length polypeptide produced by the appropriate Eimeria gene. The complete protein may be obtained by purification from the appropriate species of Eimeria, or by expression in an appropriate expression vector of the corresponding recombinant derived gene product. Protein fragments or subunits refers to any portion of the protein which contains fewer amino acids than the complete protein and retains the ability to induce anti-coccidial immunity. Hybrid proteins include, but are not limited to, fusion proteins or proteins resulting from the expression of multiple genes within the expression vector. A fusion protein is defined as one in which a limited number of amino acids coded for by the expression vector are expressed and the expression results in their attachment to the specific immunogenic polypeptide. Proteins resulting from multiple genes may include the specific immunogenic polypeptide linked to a second polypeptide or peptides by peptide bonds that enhance immune reactivity. The enhancing polypeptide portion may have the capability of increasing the immune response to the coccidial immunogen.

Pharmaceutically useful compositions comprising the DNA or proteins encoded by the DNA may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein The pharmaceutical compositions may be provided to the individual by a variety of routes such as subcutaneous, topical, oral, mucosal, intravenous and intramuscular.

The vaccines of the invention comprise DNA, RNA or proteins encoded by the DNA that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally, intravenously or intramuscularly. The dosage administered may vary with the condition, sex, weight, and age of the individual as well as the route of administration. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The vaccine may be administered in single or multiple doses.

The purified proteins of the present invention may be used in the formulation of immunogenic compositions. Such compositions, when introduced into a suitable host, are capable of inducing an immune response in the host.

The purified proteins of the invention or derivatives thereof may be used to generate antibodies. The term "antibody" as used herein includes both polyclonal and monoclonal antibodies, as well as fragments thereof, such as, Fv, Fab and F(ab)2 fragments that are capable of binding antigen or hapten.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis.

The cloned DNA or fragments thereof obtained through the methods described herein may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are fully described in Sambrook, J., et al., supra, and are known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells. Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express the cloned DNA or fragments thereof in mammalian cells. A variety of bacterial expression vectors may be used to express the cloned DNA or fragments thereof in bacterial cells. A variety of fungal cell expression vectors may be used to express the cloned DNA or fragments thereof in fungal cells. A variety of insect cell expression vectors may be used to express the cloned DNA or fragments thereof in insect cells.

An expression vector containing the cloned DNA or fragments thereof may be used for expression of proteins or fragments of the proteins in a cell, tissue, organ, or animal. Animal, as used herein, includes humans. Host cells may be prokaryotic or eukaryotic, including but not limited to bacteria such as *E. coli,* fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce the cloned protein. Identification of expressing host cell clones may be done by several means, including but not limited to immunological reactivity with specific antibodies. Following expression of the recombinant protein in a host cell, the protein may be recovered to provide purified protein.

Advantageously, compounds of the present invention may be administered in a single dose, or the total dosage may be administered in several divided doses. Furthermore, compounds for the present invention may be administered via a variety of routes including but not limited to intranasally, transdermally, by suppository, orally, and the like.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the bird. A veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and may be administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, nontoxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth, sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

*E. tenella* oocysts are isolated from the cecal contents of chickens infected 4 to 10 days earlier, preferably 7 days, while *E. acervulina* oocysts are isolated from feces and intestinal contents of chickens infected 5 to 6 days earlier. The cecal contents and feces are individually physically disrupted in a Waring Blender, in distilled water and digested with a proteolytic enzyme, preferably pepsin. Debris and pepsin are removed by centrifugation in distilled water. A partially pure oocyst fraction is collected by flotation in about 2.2M sucrose, Jackson, Parasitol. 54:87–93 (1964), and further treated by incubation in sodium hypochlorite at a concentration of about 5 to about 6 percent, preferably 5.25%, in water at about 4° C. for approximately 10 minutes. The sodium hypochlorite is removed by several washes in sterile phosphate buffered saline (PBS) at about pH 7.6 to obtain purified, sterile oocysts. Oocysts are allowed to sporulate in a shaking water bath for about 48 hours at about 20° C., Edgar, Trans. Am. Micr. Soc. 62:237–242 (1954).

Sporulated oocysts are suspended in PBS and disrupted in a Bransonic cell disrupter (Branson), with a tapered probe at about 0° C. Sonication is carried out with short bursts, about 30 seconds, to prevent overheating, with 90 percent breakage occurring within about 5 to about 20 minutes. A detergent is added to the sonicate, preferably Zwittergent 3-12 (Calbiochem) about 0.1% w/v and the mixture is stirred at about 4° C. for about 18 hours. The detergent treated sporulated oocyst preparation is centrifuged at about 27,000×g for about 30 minutes and the supernatant fluid collected.

Sporozoites are prepared by grinding a suspension of purified sporulated oocysts, about $5 \times 10^7$/ml in PBS, at about pH 7.6, at about 500 rpm for about 5 minutes at about 4° C. in a tissue homogenizer with a loose-fitting pestle following the procedure of Patton, Science 150:767–769 (1965). The *E. tenella* disrupted material is collected by centrifugation. The pellet consists of unbroken oocysts, sporocysts and oocyst shells which is resuspended in an excysting solution containing about 0.25% (w/v) trypsin and about 4% (w/v) taurodeoxycholic acid (Sigma) in a buffered solution such as Hanks balanced salt solution (pH 7.4). The *E. acervulina* pellet, also composed of unbroken oocysts, sporocysts and oocyst shells, was resuspended in an excysting solution containing about 0.125% (w/v) trypsin (1:250) and about 1.0% taurodeoxycholic acid in a buffered solution such as Hank's Balanced salt solution (pH 7.4). The resuspended pellets are incubated at about 41° C. in an atmosphere containing about 5% $CO_2$. Excysting was allowed to continue for about ½ hour for *E. acervulina* and about 1 hour for *E. tenella* after which time the solutions are removed by centrifugation. Sporozoites are isolated using a DE-52 anion exchange column employing the method of Schmatz, et al. J. Protozool. 31:181–183 (1984). Purified sporozoites are disrupted by freezing and thawing at least 3 times, and sonicated until disrupted in PBS containing about 1 mM phenylmethylsulfonylfluoride.

Both the sporulated oocyst and the sporozoite cell-free preparations are separated by gel permeation chromatography, preferably Sephadex S-200 (Pharmacia) in a separation buffer containing about 50 mM $Na_2HPO_4$—$NaH_2PO_4$, pH about 7.2 and about 0.1% Zwittergent 3-12. Each preparation is added to the columnn, about 8×44 cm and eluted with the separation buffer. Elution is monitored by absorbance at 230 nm and the fractions, about 14 ml per fraction, collected. The fractions are analyzed by linear gradient sodium dodecyl sulfate (SDS) polyacrylamide gel electrophoresis (SDS-PAGE) and the fractions pooled according to these profiles. Pooled fractions were dialyzed against a bicarbonate buffer and tested for their ability to protect chickens against challenge with infective E. tenella sporulated oocysts. Two day old broiler pullets are immunized intramuscularly with pooled fractions of sporulated oocyst or sporozoite cell free immunogens, about 5 μg to about 50 μg protein in PBS. The cell-free immunogen is precipitated to alum (about 0.4% final concentration) in a total volume of about 0.12 ml per dose per bird. The alum-immunogen precipitation complex is prepared by the technique of Weir, Handbook of Experimental Immunology, Blackwell Scientific Publications, London, pg. A3.11 (1978). Immunization was repeated at days nine and sixteen and the birds are challenged on day 23, seven days after the final immunization, with infective E. tenella sporulated oocysts. A single fraction from each preparation protected the chickens from sporozoite challenge. These fractions had similar elution and electrophoresis profiles suggesting that the polypeptides may be similar. The most active immunogenic fraction isolated from sporulated oocysts is found in column fractions 84–94 and is designated Fraction V.

Antiserum is produced against the immunoprotective fractions of E. tenella sporulated oocysts (Fraction V), sporozoites, sonicated unsporulated oocysts, second generation schizonts and E. acervulina sonicated sporozoites. The E. tenella schizonts are prepared from chicken intestinal cells about four days post-infection according to the protocol of James, Parasitol. 80:301–312 (1980). Blood is collected from the antibody producing animals, preferably rabbits, prior to initiation of the immunization procedure and the preimmune serum is isolated and stored for control purposes. The rabbits are given multiple immunization injections with one of the above described immunogens, about 20 μg to about 80 μg of protein per immunization. The initial immunization is given with an acceptable adjuvant, generally equal volumes of immunogen and adjuvant. Acceptable adjuvants include Freund's complete, Freund's incomplete, alum-precipitate, water-in-oil emulsion containing *Corynebacterium parvum* and tRNA, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art. The anti-coccidial antisera are characterized by serological analysis, preferably Western blot analysis using antigens obtained from unsporulated oocysts, sporulated oocysts, sporozoites and schizonts.

The parasite immunogens to be used for Western blot analysis, about 50 μg, as described above, are mixed in about equal volumes with about 2× concentrated sample buffer consisting of about 0.1M Tris HCl, about pH 6.8, about 4% sodium dodecyl sulfate (SDS), about 20% (v/v) glycerol, about 10% (v/v) 2-mercaptoethanol, and about 0.002% (v/v) bromophenol blue. The samples are boiled for about 3 minutes and electrophoresed on a 5–20% linear gradient of polyacrylamide gel (PAGE) containing SDS by the method of Laemmli, Nature 227:680–684 (1970). The proteins separated by SDS-PAGE are electrophoretically transferred to nitrocellulose by the method of Towbin, et al., Proc. Natl. Acad. Sci. U.S.A. 76:4350–4354 (1979), and the nitrocellulose is blocked with 0.5% gelatin in phosphate buffered saline about pH 7.4. The blocked nitrocellulose is incubated overnight at room temperature in about 20 ml of the appropriate antiserum diluted about 1:5 to 1:400 in TEN buffer (about 50 mM Tris-HCl, about 150 mM NaCl and about 5 mM ethylenediamine tetraacetic acid (EDTA) at a pH of about 7.4) containing about 0.25% gelatin and 0.05% Triton X-100. Bound antibody is detected by the addition of 125I-protein A.

The appropriate coccidial DNA is isolated and identified by reacting the gene derived protein with anti-Fraction V and anti-sporozoite antibodies. Recombinant coccidial polypeptides are produced by cloning the natural gene from either genomic DNA or cDNA. Genomic DNA, a preferred method of obtaining specific genes, is extracted from sporocysts or sporozoites by disrupting the parasites, about $1.5 \times 10^8$, by treatment with about 0.5% SDS and about 15 mM EDTA. The released DNA is solubilized by digestion with a proteolytic enzyme, preferably Proteinase K, about 100 mg/ml at about 50° C. for about 3 hours. Genomic DNA is purified by about two extractions with phenol, about two extractions with a mixture of phenol, chloroform and isoamyl alcohol (about 25:24:1), about two extractions with chloroform and isoamyl alcohol (about 24:1 ) and about two successive precipitations with sodium acetate/ethanol. The DNA is washed twice with about 70% ethanol and resuspended in Tris-HCl, about 10 mM and EDTA, about 1 mM (TE) at the approximate concentration of about 5×108 parasite equivalents per ml. Any associated RNA is selectively removed by digestion with RNase, preferably heat inactivated RNase A, at a concentration of about 50 μg/ml for about 60 minutes at about 37° C. The RNase A and any other residual proteins are removed by a secondary digestion with Proteinase K in about 0.5% SDS/15 mM EDTA for about 3 hours at about 50° C. The genomic DNA is then extracted with organic solvents, precipitated with ethanol and washed with about 70% ethanol and collected by centrifugation. The genomic DNA pellet is suspended in TE at a concentration of about $2-3 \times 10^9$ sporozoite equivalents/ ml and quantitated by absorbance at 260 nm. Coccidial DNA is prepared for cloning by either physical or chemical fragmentation of high molecular weight DNA. The genomic DNA is then incorporated into an appropriate cloning vector. The cloning vectors are transduced into a host cell and screened by a procedure similar to that of Huynh, et al., In "DNA cloning: A practical approach", Vol. I, Glover Ed., IRL Press Oxford, pp. 49–78 (1985). Positive clones are transferred to expression vectors engineered for high volume production of the desired immunogenic protein. The expression vectors are transformed into suitable host cells for the production of immunogenic protein.

A preferred process for obtaining genetic information for the production of coccidial immunogenic polypeptides is the isolation of mRNA coding for a specific protein. Total RNA is isolated from oocysts, sporulated for about seven hours, and sporozoites using the guanidinium thiocyanate method of Chirgwin, et al., Biochem. 18:5294–5299 (1979). Polyadenylated RNA is selected by oligo (dT)-cellulose chromatography, Aviv and Leder, Proc. Nat. Acad. Sci. U.S.A. 69:1408–1412 (1972). Utilizing the polyadenylated RNA, about 6 to about 9 μg, first and second-strand cDNA reactions are performed using a reverse transcriptase such as AMV-reverse transcriptase, a RNase such as RNase H and a DNA polymerase such as DNA polymerase I following the procedure described by Gubler and Hoffman, Gene 25:263–269 (1983). The cDNA is methylated with a methylase such as Eco RI methylase, blunt-ended with a polymerase such as T4 DNA polymerase and ligated to phosphorylated oligonucleotide linkers such as Eco RI dexanucleotide linkers with a DNA ligase such as T4 DNA ligase. The linker ligated cDNAs are digested to completion with a restriction enzyme such as EcoRI and the digested linkers removed by repeated precipitations with absolute ethanol out of 2M ammonium acetate, Okayama and Berg, Mol. Cell. Biol. 2:161–170 (1982). The cDNA was further purified on an Elutip-d colunm (Schleicher & Schell). Restriction enzymes or restriction endonucleases are enzymes that recognize specific nucleotide base sequences within double-stranded at a specific location witands at a specific location within the recognition sequence. The purified cDNA, about 100 ng to about 500 ng, with 300 ng being preferred, is ligated into about 7.5 mg of commercially purchased, EcoRI-digested, alkaline phosphatase treated ggt11 vector DNA and packaged in vitro with commercially available packaging extracts according to the manufacturer's instructions (Amersham). Other acceptable vectors can be used, but ggt11 is preferred because it allows the inducible expression of Eimeria antigens in *E. coli* as β-galactosidase fusion proteins. Aliquots of the packaged phage are transduced into *Escherichia coli* host strain Y1088 and these are plated on Luria-Bertani (LB) medium agar plates using about 2.5 ml LB soft agar containing about 600 $\mu$g/ml X-gal (5-bromo-4-chloro-3-indolyl-β-D-galactopyranoside) and about 16 mM isopropyl-β-D-thiogalactopyranoside (IPTG).

A cDNA library consisting of approximately $1\times10^7$ independent recombinant phage clones is generated. The non-recombinant background, as determined by growth on X-gal/IPTG plates, is estimated to be about 13%.

Screening of the cDNA library is accomplished by the method of Huynh, et al. "In: DNA Cloning: A Practical Approach", Vol. I, Glover, Ed., IRL Press, Oxford, pp. 49–78 (1985). Packaged phage from the unamplified cDNA library were transduced into *E. coli* strain Y 1090 as described by Huynh, supra, and plated at an appropriate density, about 0.5 to about $1.0\times10^5$ plaque forming units (pfu) per plate. The plates are incubated, at about 42° C. for about 3 hours, overlaid with nitrocellulose filters presoaked in about 10 mM IPTG, and reincubated overnight at about 37° C. The filters are removed, blocked with about 20% fetal calf serum in an acceptable buffer, such as Tris buffered saline (TBS) (about 50 mM Tris-HCl about 150 mM NaCl, at a pH of about 8.0) containing about 0.05% Tween 20 (TBST), and incubated with the appropriate antibody, generally rabbit anti-sporozoite antibody or rabbit anti-Fraction V antibody, diluted about 1:100 in TBST containing about 20% fetal calf serum for an appropriate length of time. All antisera are exhaustively preabsorbed with a concentrated lysate of lambda gt11 lysogen BNN93. Antibody binding sites are detected by contacting the filters with $^{125}$I-protein A. Positive plaques are picked, replated, and rescreened until each clone is shown to be plaque pure. An initial screen of the sporulated oocyst library of about $1\times10^6$ independent recombinants with rabbit anti-sporozoite antibody results in the isolation of about 57 antigen expressing phage. Secondary and tertiary rescreening reveals that greater than 29% of the clones initially identified remain positive.

Cross-screening involves the spotting of about 1 $\mu$l of phage lysate from each plaque purified clone on a lawn of *E. coli* Y1090 cells with recombinant fusion proteins being induced as previously described. The proteins are transferred to nitrocellulose and innmunoblotted as described above. The cross-screening antisera include rabbit anti-*E. tenella* unsporulated oocyst antibody, rabbit anti-*E. tenella* sporozoite antibody, rabbit anti-Fraction V and rabbit anti-*E. tenella* schizont antibody. All antisera are exhaustively preabsorbed with a concentrated lysate of λgt11 lysogen BNN93.

Recombinant and wild type λgt11 phage are introduced as lysogens into *E. coli* host strain Y 1089 at a multiplicity of about 10. Lysogenized clones are grown in about 10 ml of Luria-Bertani (LB) medium supplemented with about 50 $\mu$g/ml ampicillin at about 32° until an optical density at 600 nm of 0.25 is reached. Phage replication is induced by a temperature shift to about 45° C. for about 20 minutes and the synthesis of β-galactosidase fusion proteins is induced by the addition of about 10 mM IPTG to the culture medium. The cells are incubated and collected by centrifugation and the pellets are resuspended in about 250 ml of NET buffer, about 50 mM Tris-HCl, pH about 7.5, about 150 mM NaCl, about 5 mM ethylenediaminetetraacetic acid (EDTA), with about 2% SDS. The cells are lysed by boiling and the bacterial DNA is removed by centrifugation. The supernatant fluids are analyzed on about 5% SDS-PAGE under denaturing conditions. Duplicate gels are run with one being stained with silver stain (Biorad) and the other immunoblotted by the method of Towbin, et al., Proc. Natl. Acad. Sci. U.S.A. 76:4350–4354 (1979).

Monospecific antibodies to each of the recombinant immunogens are affinity purified from polyspecific antisera by a modification of the method of Hall, et al., Nature 311:379–382 (1984), prepared by immunizing rabbits as described above with purified recombinant *E. tenella* proteins as described below or prepared as monoclonal antibodies using the technique of Kohler and Milstein, Nature 256:495–497 (1975). The Hall technique of preparing monospecific antibodies from polyclonal antiserum requires the preparation of filter plaque lifts from purified recombinant clones as is done for screening. Approximately $2\times10^5$ plaque forming units are plated to give close to semiconfluent lysis at the end of the 37° C. incubation period. The nitrocellulose is removed from the plates and is blocked with about 20% fetal calf serum in TBST for about 4 hours and incubated overnight with about 20 ml of the preabsorbed polyspecific serum, diluted about 1:200 with about 20% fetal calf serum in TBST containing about 0.02% NaN$_3$. The filters are washed at least 5 times with about 50 ml TBST for at least 20 minutes and 1 time with about 0.15 mM NaCl and about 0.05% Tween 20. The antibodies are eluted with an acceptable eluant, such as about 0.2M glycine-HCl, about 0.15M NaCl and about 0.05% Tween 20, at a pH of about 2.8 for about 30 minutes. The pH is adjusted to about 8.0 and the antibodies are stored.

Monoclonal antibody reactive against each of the recombinant *E. tenella* group immunogens, antigens or epitopes is prepared by immunizing inbred mice, preferably Balb/c with the appropriate recombinant protein. The mice are immunized intraperitoneally with about 100 ng to about 10 $\mu$g, preferably about 1 $\mu$g recombinant immunogen per 0.5 ml in an equal volume of an acceptable adjuvant. Such acceptable adjuvants include, but are not limited to, Freund's complete, Freund's incomplete, alum-precipitate, water-in-oil emulsion containing *Corynebacterium parvum* and tRNA. The mice are given intravenous booster immunizations of an equal amount of recombinant immunogen without adjuvant at about days 14, 21, and 63 post primary immunization. At about day three after the final booster immunization individual mice are serologically tested for anti-recombinant immunogen antibody. Spleen cells from antibody producing mice are isolated and fused with murine myeloma cells, such as SP-2/0 or the like, by techniques known to the art, see Kohler and Milstein, Nature 256: 495–497 (1975). Hybridoma cells are selected by growth in hypoxanthine, thymidine and aminopterin in an appropriate cell culture medium such as Dulbecco's modified Eagle's medium (DMEM).

Antibody producing hybridomas are cloned, preferably using the soft agar technique of MacPherson, Soft Agar Techniques, in Tissue Culture Methods and Applications, Kruse and Paterson, Eds. Academic Press, p. 276 (1973). Discrete colonies are transferred into individual wells of culture plates for cultivation in an appropriate culture medium. Antibody producing cells are identified by screening with the appropriate E. tenella recombinant immunogen. Immunogen positive hybridoma cells are maintained by techniques known in the art. Specific anti-recombinant E. tenella monoclonal antibodies are produced by cultivating the hybridomas in vitro or preparing ascites fluid in mice following hybridoma injection by procedures known in the art.

The parasite antigens are assayed by Western blot analysis as described above. The clones of interest may be placed into four antigenic groups, according to the reaction of the expressed polypeptides with the above described antisera. Different clones of the same group express portions of the same polypeptide, as judged by antibody reactivity, DNA cross-hybridization, and restriction endonuclease mapping.

phenol, phenol/chloroform/isoamyl alcohol and chloroform/-isoamyl alcohol. The DNA is precipitated with sodium acetate/ethanol, washed with ethanol and air dried. An aliquot of each DNA is analyzed on an analytical agarose gel for confirmation.

Expression of the genes coding for the protective coccidial immunogens is accomplished in a number of different host cells with a variety of promoter-expression systems. The host cells include bacteria, yeast, insect, and mammalian cells. The antigens may also be expressed in a number of virus systems. Although the genes can be expressed in numerous procaryotic cells and various eucaryotic cells the most preferred host cell is $Escherichia\ coli$. The expression vectors which can be used for the expression of the protective immunogens include, but are not limited to, pBR322, pPLa2311, pKC30, ptac12, ggt11, pAS1, pLC24, pSB226, pRIT2T and SV40 with a CheY-pUC derived vector designated pJC264 being preferred. It is desired and intended that there be included in this invention, the use of E. tenella immunogens, which are native proteins or fragments thereof, recombinant proteins or fragments thereof, or fusion

TABLE 1

IMMUNE REACTIVITY OF ISOLATED CLONE PRODUCTS

| CLONE | ANTI FRACTION V | ANTI-E.t. UNSPORULATED OOCYST | ANTI-E.t. SPOROZOITE | ANTI-E.t. SCHIZONT | ANTI-E.a. SPOROZOITE |
|---|---|---|---|---|---|
| A | + | + | + | = | + |
| B | + | − | + | − | + |
| C | + | − | + | − | − |
| H | + | − | + | n.d. | − |
| F | + | n.d. | n.d. | n.d. | n.d. |

E.t. denotes E. tenella while E.a. denotes E. acervulina. A (+) denotes that the antibody can react with the specific recombinant derived protein while a (−) denotes a lack of such a response and n.d. means not done.

Purification of the cDNA inserts from λgt11 clones is accomplished by cutting the recombinant phage DNA to completion with EcoRI, about five fold enzyme excess, in a reaction buffer composed of about 50 mM NaCl/about 100 mM Tris-HCl, about pH 7.5, about 5 mM $MgCl_2$. The reaction products are adjusted to about 0.3M sodium acetate by the addition of about one-tenth volume of a 3M (pH 5.6) stock solution, precipitated with ethanol, chilled and collected by centrifugation. After suspending the pellet in TE, the DNA is electrophoresed in agarose containing ethidium bromide to resolve the insert from the phage arms.

Fractionation of the inserts is verified by visualization under ultraviolet light. The inserts are electrophoresed onto NA-45 (Schleicher & Schuell) membranes and then eluted from the membranes. Insoluble particles are removed by centrifugation and the soluble material is extracted with proteins linked to other proteins which may or may not enhance the Eimeria peptides immunogenicity. The fusion immunogens may be designed in such a manner that the immunogenic expression protein contains an additional polypeptide portion encoded for by the expression-plasmid or an additional peptide portion that has been added to the gene by the inclusion of an additional DNA base sequence. The pJC264 plasmid is designed to include the expression of an 88 amino acid portion of the E. coli CheY protein operably attached to 5 linker amino acids linked or fused to the various E. tenella peptides. Operably attached refers to an appropriate sequential arrangement of nucleotide segments, linkers, or genes such that the desired protein will be produced by cells containing an expression vector containing the operably attached genes, segments or linkers. The nucleotide sequence of the CheY gene and the amino acid sequence produced from the gene are shown in the following table.

TABLE 2

Amino Acid and Nucleotide Sequences of the Che Y Protein

```
              10          20          30          40          50
              *           *           *           *           *
ATG GCG GAT AAA GAA CTT AAA TTT TTG GTT GTG GAT GAC TTT TCC ACC ATG CGA
MET ALA ASP LYS GLU LEU LYS PHE LEU VAL VAL ASP ASP PHE SER THR MET ARG
```

TABLE 2-continued

Amino Acid and Nucleotide Sequences of the Che Y Protein

```
              60                        70                        80                        90                       100
              *                         *                         *                         *                         *
CGC  ATA  GTG  CGT  AAC  CTG  CTG  AAA  GAG  CTG  GGA  TTC  AAT  AAT  GTT  GAG  GAA  GCG
ARG  ILE  VAL  ARG  ASN  LEU  LEU  LYS  GLU  LEU  GLY  PHE  ASN  ASN  VAL  GLU  GLU  ALA
         20                                                           30
      110                      120                       130                       140                      150                       160
       *                        *                         *                         *                        *                         *
GAA  GAT  GGC  GTC  GAC  GCT  CTC  AAT  AAG  TTG  CAG  GCA  GGC  GGT  TAT  GGA  TTT  GTT
GLU  ASP  GLY  VAL  ASP  ALA  LEU  ASN  LYS  LEU  GLN  ALA  GLY  GLY  TYR  GLY  PHE  VAL
                   40                                                                      50
                  170                       180                       190                       200                       210
                   *                         *                         *                         *                         *
ATC  TCC  GAC  TGG  AAC  ATG  CCC  AAC  ATG  GAT  GGC  CTG  GAA  TTG  CTG  AAA  ACA  ATT
ILE  SER  ASP  TRP  ASN  MET  PRO  ASN  MET  ASP  GLY  LEU  GLU  LEU  LEU  LYS  THR  ILE
                             60                                                                     70
     220                      230                       240                       250                      260
      *                        *                         *                         *                        *
CGT  GCG  GAT  GGC  GCG  ATG  TCG  GCA  TTG  CCA  GTG  TTA  ATG  GTG  ACT  GCA
ARG  ALA  ASP  GLY  ALA  MET  SER  ALA  LEU  PRO  VAL  LEU  MET  VAL  THR  ALA
                                       80
```

Linker amino acids are defined herein as those amino acids used to link an E. tenella defined gene, one which produces a native protein, to a fusion protein. Any amino acid or group of amino acids may be used as linkers, however, the preferred amino acid sequence and nucleotide sequence of the peptide linking the CheY protein to the E. tenella protein is:

5' GCC CAA GAA TTC GGN 3' ALA GLN GLU PHE GLY

The 3' terminal N constitutes the first nucleotide of the cDNA and may represent any nucleotide with the resultant amino acid always being glycine.

The preferred plasmid pJC264 is derived from the plasmid pJC220 which is in turn derived from a construct containing a portion of the E. coli chemotaxis gene, CheY, and the gene for rat atrial natriuretic factor (ANF). The CheY-ANF plasmid is constructed from the pLC1-28, Col E1-derived plasmid described in Matsumura, et al., J. Bacteriol 160: 36–41 (1984). The Che operon fragment containing CheY and CheZ genes is excised from the pLC1-28 plasmid as a BamHI-HindIII fragment and subcloned into a BamHI-HindIII digested pUC13 plasmid (PL Biochemicals) to give a pUC13-CheY-CheZ plasmid. *Escherichia coli* JM105 clones transformed by pUC13-CheY-CheZ express CheY and CheZ polypeptides off the lac promoter contributed by the pUC13 vector, Davis, et al., Basic Methods In Molecular Biology, Elsevier, New York, N.Y., pg. 30 (1986). The pUC13-CheY-CheZ plasmid is digested at the unique PstI site internal to the CheY coding region, see Matsumura, et al., supra, and at the unique SmaI site in the pUC13 polylinker 3' to the inserted Che DNA. The resulting 3 kb PstI-SmaI fragment containing the pUC13 vector and the DNA encoding the N-terminal 100 residues of CheY was recombined with the 160 bp PstI-HindHIII fragment of pSCN1-(rat-ANF-26) that encodes the Met-(rat-ANF-26) sequence and contains 50 bp of untranslated RAS1 sequence 3' to the termination codon for the ANF peptide. This expression vector is termed the CheY-ANF vector. The pSCN1-(rat-ANF-26) fusion plasmid is constructed from the pSCN1 plasmid which expresses the N-terminal 165 amino acids of the yeast RAS1 protein SC1N, Temeles, et al., Nature 313: 700–703 (1985). Plasmid pSC1N is digested to completion with AccI, and the ends are filled in with E. coli DNA polymerase I large fragment (Kienow polymerase). A synthetic ANF gene is ligated to pSC1N and used to transform competent E. coli JM105 cells. The nucleotide sequence of the CheY-ANF plasmid from the EcoRI restriction site to the first HindIII restriction site prior to the CheY fragment is identical to that shown for pUC19 by Yanisch-Perron, et al., Gene 33: 103–119 (1985).

Figure 7:
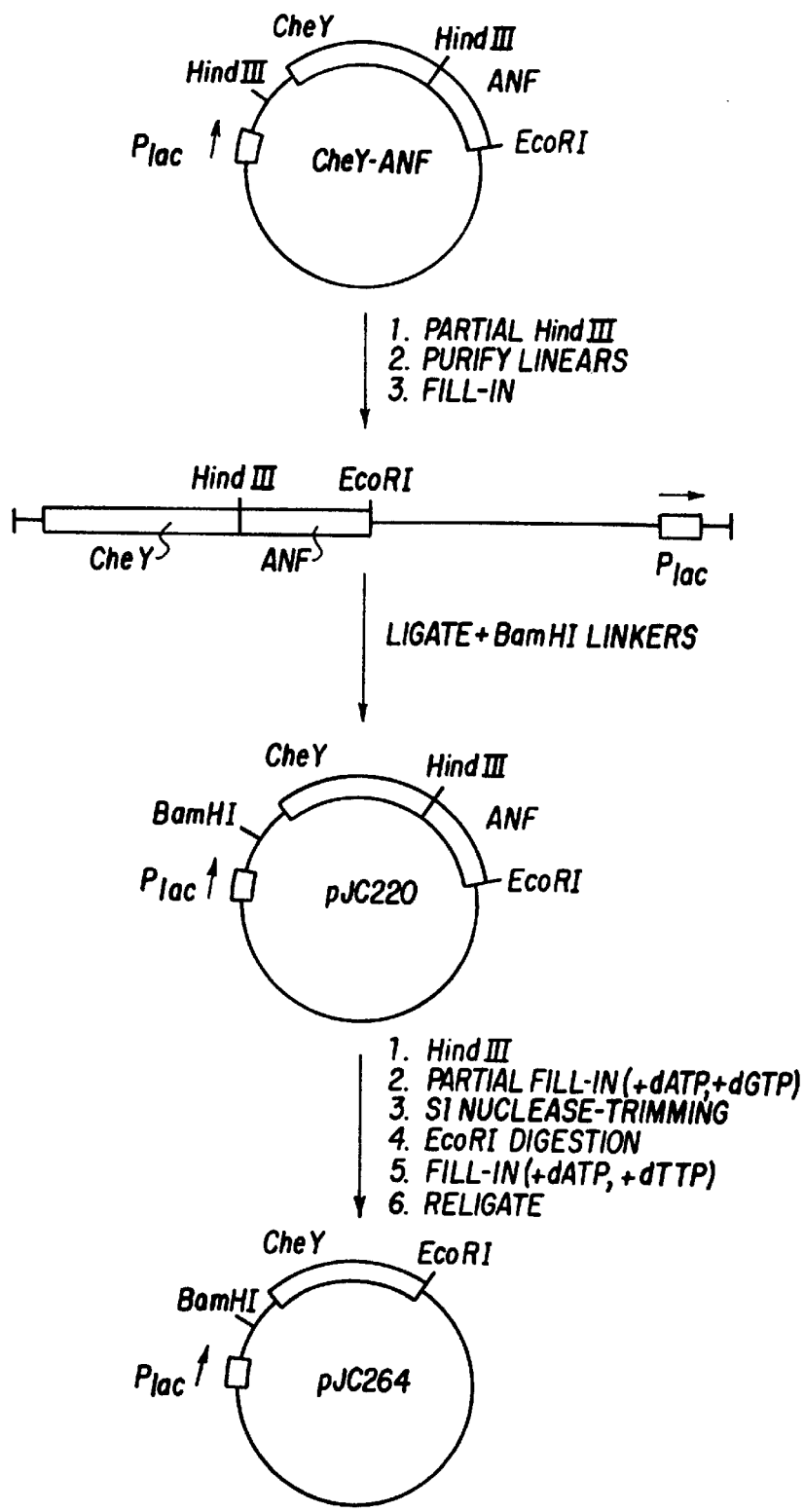
FIG. 7 illustrates the conversion of the CheY-ANF plasmid to the pJC264 plasmid.
Figure 8:
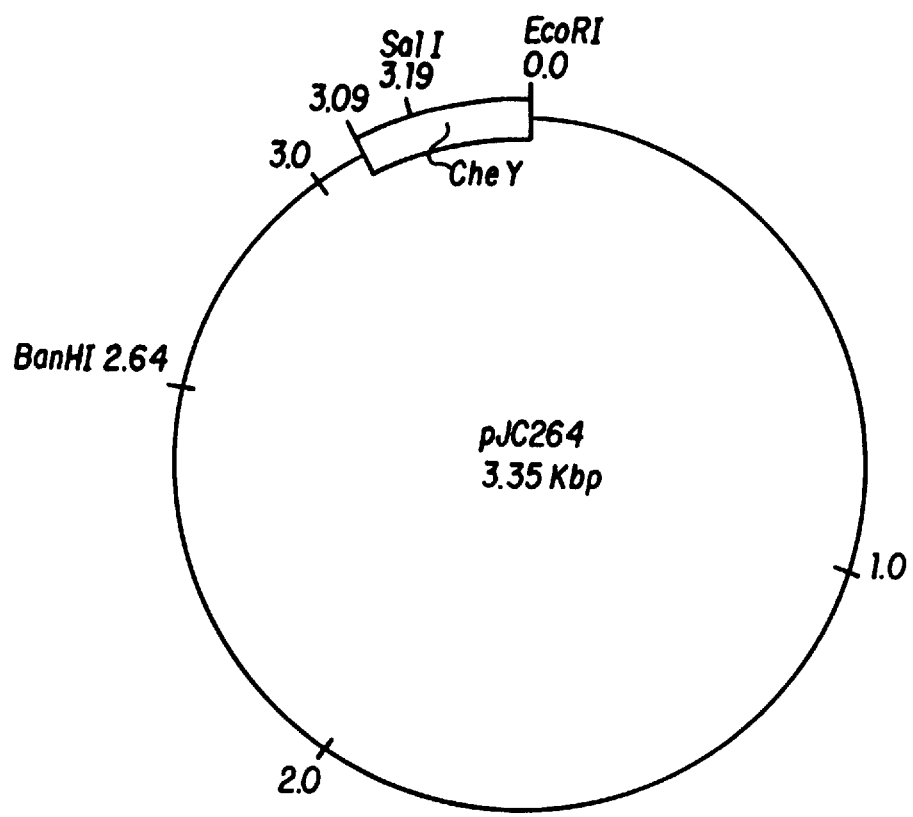
FIG. 8 is a restriction map of the pJC264 plasmid.

The pJC264 expression plasmid contains a unique EcoRI site, in the same reading frame as the lambda gt11 EcoRI site, which permits easy subcloning and expression of EcoRI fragments from lambda gt11 expression libraries. The inclusion of a portion of the CheY gene product in the resulting fusion protein may facilitate stabilization of the protein and enhance the purification of the protein. The small size of the CheY protein compared with other fusion carriers such as β-galatosidase, permits a more favorable molar yield of the protein of interest for a given mass of fusion protein. The CheY containing plasmid pJC264 results in high expression levels of fusion proteins with the first 93 amino acids of the amino terminus being derived from the E. coli CheY protein and linkers. As noted above the pJC264 plasmid is derived from the CheY-ANF plasmid as shown in FIG. 7. CheY-ANF is partially digested with HindIII and electrophoresed in about 0.7% Seaplaque agarose gel. Full-length linear DNA is mechanically excised, removed from the gel by melting, purified on a NACS column (BRL) and recovered by ethanol precipitation. The DNA fragment is made blunt by filling in the HindIII ends with the Klenow fragment of DNA Polymerase I (Boehringer Mannheim), phenol-extracted and ethanol precipitated. BamHI linkers phosphorylated at the 5' position are ligated to the purified DNA, and E. coli HB 101 is transformed directly with the ligation mix. Ampicillin-resistant transformant colonies are restriction-mapped for the BamHI linker. A colony designated pJC220 contains the BamHI linker in place of the promoter-proximal HindIII site. The plasmid now has a HindIII site at the 3' end of the CheY coding region and is therefore unique. Plasmid pJC220 is digested with HindIII and two bases of the four-base overhang are filled in with the Klenow fragment of DNA Polymerase I in the presence of dATP and dGTP. The remaining two bases of the overhang are removed with S1 nuclease, leaving a blunt end. The DNA is then digested with EcoRI and filled in with the Klenow fragment of DNA Polymerase I in the presence of dATP and dTTP. The plasmid is recircularized by blunt-end ligation with T4 DNA ligase to yield pJC264, which contains a unique EcoRI site at the 3' end of the CheY coding region. The new EcoRI site is in the same reading frame as the EcoRI site of lambda gt11, permitting direct subcloning and expression, as CheY fusion proteins, of antigens identified by expression in lambda gt11 libraries. The pJC264 restriction map is shown in FIG. 8.

Minipreps of recombinant λgt11 bacteria-phage are prepared and phage DNA is isolated. The gene insert for each antigen is removed by EcoRI digestion and fractionated from the phage arms by agarose gel electrophoresis. The genes are then inserted into the plasmid pJC264 which has been linearized at its unique EcoRI site and phosphatased to decrease the efficiency of autoligation. Ligation products are then transfected into the bacterial host, E. coli JM83 using standard $CaCl_2$ methods known in the art and the transformants are selected on ampicillin plates. Ampicillin resistant colonies are grown on an analytical scale to score for the presence of an insert, score for orientation of the foreign DNA with respect to the bacterial promoter and score for expression of bacterial fusion proteins by Western blot analysis, using polyclonal antisera raised against E. tenella immunogens.

DNA inserts are isolated from phage clones representative of the various immunogen groups identified above and are also sub-cloned into the puc18 plasmid-vector as described above for the CheY vector, pJC264. Restriction endonuclease maps of members of each group are prepared. The following table contains the groups, clone designation within each group and the restriction endonucleases which are unable to cut within the clone insert.

TABLE 3

RESTRICTION ENDONUCLEASE
SITES ABSENT FROM DESIGNATED CLONES

| Group | Clone Designation | Restriction Endonucleases |
|---|---|---|
| A | SO6' | BamHI, HindIII, KpnI, NcoI, |
|   | SP1 | AvaI, ClaI, XhoI, SalI, |
|   | SO67 | SstI, SstII, XbaI, BglI, |
| B | SO9 | BamHI, HincII, KpnI, |
|   | SO24 | NcoI, ClaI, SalI, SstI, |
|   | SO7' and SO7 | XbaI |
|   | SO1' |   |
| C | SP54 | BamHI, KpnI, HincII, |
|   | SP59 | NcoI, ClaI, PvuII, |
|   |   | XhoI, SalI, SstI, SstII, |
|   |   | XbaI, BglI |
| H | SO311 | BamHI, HindIII, KpnI, |
|   | SO227 | AvaII, ApaI, NcoI, |
|   | SO231 | AvaI, ClaI, PstI, XhoI, |
|   |   | SalI, SstII, XbaI |
| F | SO216 | ApaI, AvaI, AvaII, BamHI, BglI, |
|   |   | ClaI, HincII, NcoI, PstI, PvuII, |
|   |   | SalI, SstI, SstII, XbaI, XhoI |

Some restriction endonucleases are capable of cleaving one or more clones within a group but not all clones. In the B group, additional restriction endonucleases which cleave at least one of the four clones include AvaI, PstI, SstII. These sites have not been mapped. In the H group, the restriction endonuclease SstI does cleave within all three of the clones, but the site has not yet been mapped.

The above information is determined by growing the pUC 18 recombinant plasmids as mini-preparations in LB broth and isolating the DNA using the alkaline lysis method described below. The DNA is resuspended in digestion buffer such as TE buffer which contains, about 10 mM Tris-HCl (about pH 8.0), about 1 mM EDTA (about pH 8.0), containing DNase-free pancreatic RNase, about 20 μg/ml and mixed on a Vortex mixer briefly. The DNA samples are then digested with a variety of restriction endonucleases (available from Bethesda Research Laboratories) to determine which had the ability to cleave the cDNA inserts. A mapping analysis is conducted by doing single and double digests of the insert/plasmid. DNA fragments are separated electrophoretically on about 1% agarose gels, and sized by comparison to DNA markers which are run simultaneously on the same gels. Maps are constructed of each clone by entering the fragment size data and known vector restriction sites into the Intelligenetics Restriction Map Generator program (MAP, Intelligenetics, Inc.). The derived location along the nucleotide sequence of the enzymatic cleavage sites is accurate to about the ±10% level.

Production of recombinant immunogenic coccidial proteins, recombinant fusion proteins and recombinant CheY fusion proteins, with recombinant CheY fusion proteins being preferred, is accomplished by overnight culturing, in 2×YT medium containing ampicillin, of selected recombinant bacteria isolated from a single colony. The overnight culture is used to inoculate about 500 ml of 2×YT plus ampicillin. The culture is grown at about 37° C. with aeration until the mid-logarithmic phase of growth is reached, at which time IPTG is added to a final concentration of about 100 mM. The cells are incubated for about another 3 to 4 hours, chilled on ice and collected by centrifugation. The cells are washed, collected by centrifugation and resuspended in about 10 ml of Buffer A which consists of about 30 mM Tris-HCl, about pH 8.0, about 5.0 mM EDTA and about 1 mM PMSF. The cell suspension is sonicated while maintained in an ice bath in three minute bursts using a Branson cell disrupter Model 350. The sonicate is clarified by centrifugation at about 27,000×g for about 45 minutes at about 4° C. This constitutes the first supernatant fluid. The pellet (P1) is washed in about 10 ml of buffer A containing 0.1% w/v Triton X- 100 for about 30 minutes in an ice-bath and recentrifuged. The supernatant fluid is collected and designated the second supernatant. The pellet (P2) is washed twice in the same buffer, buffer A. The washes are discarded. The washed pellet, P2 is then resuspended in about 1.0 ml of about 6M guanidine-HCl containing about 100 mM dithiothreitol and the suspension incubated at about 50° C. (for about 2 hours). The suspension is diluted to 10 ml with about 7M urea and is clarified by centrifugation at about 27,000×g for about 45 minutes at about 4° C. with the supernatant fluid constituting the third supernatant. Due to differences in solubility of the various fusion proteins, some are found in the first supernatant, some in the second supernatant and some are found in the third supernatant. For example, a representative clone protein from immunogen group A, SO6-CheY, was found in the first, second and third supernatants. Representative proteins from clones of group B (SO7), C (SP54), H (SO311) and F (SO216) were found in the third supernatant. Both the SO7-CheY and SP54-CheY fusion proteins were unretarded by chromatography on hydroxyapatite. The SO311-CheY fusion protein bound to hydroxyapatite, and could be eluted with 160 mM phosphate buffer. The SO6-CheY fusion protein from the third supernatant fluid was further purified by Trisacryl M-DEAE chromatography.

Representative Eimeria immunogen clones are assayed to determine the nucleotide sequence of each specific gene by one or more of three standard techniques. In some cases the nucleotide sequence of the cDNAs is determined using the chemical degradation method of Maxam and Gilbert. More routinely, the nucleotide sequence is determined by the dideoxy chain termination technique, using denatured plasmid templates (plasmid pUC18, containing assorted subsequences of the Eimeria cDNAs) as described by Hattori and Sakaki, Analyl. Biochem., 152:232–238 (1986). Finally, some nucleotide sequences are determined by subcloning the cDNA insert, or portions of it, into bacteriophage mp 18 and sequencing secreted single-stranded recombinant phage templates using the standard dideoxy chain-termination sequencing methodology of Messing. In addition to AMV reverse transcriptase and the Kienow fragment of DNA polymerase I, a modified T7 DNA polymerase has been employed.

The amino acid sequence is deduced from the determined nucleotide sequence by combining the following information. Each of the cDNAs in the phage expression vector ggt11 was identified using polyclonal antisera when expressed as a fusion protein with β-galactosidase. The fusion junction between β-galactosidase and the immunogen consists of a Glu residue linking the carboxy-terminus of β-galactosidase with a Phe residue at the N-terminus of the immunogen (within the linker region). The EcoRI restriction enzyme cleaves between the first and second nucleotide of the Glu codon when reading from the 5' to 3'. This junction (and reading frame, cloning site), at the EcoRI cleavage site, is regenerated in each subsequent cloning event involving the entire cDNA irrespective of the subcloning vector, pUC18, mp18 or pJC264. Consequently, the reading frame can be unequivocally identified and the nucleotide sequence translated once the orientation of the insert in these three vectors is established. The orientation of the cDNA insert in plasmid, pUC18 and pJC264, or phage, mp18, vectors is accomplished by restriction enzyme mapping, known in the art. Once asymmetric restriction enzyme recognition sequences are identified within the cDNA insert, insert orientation and transcriptional orientation can be unequivocally assigned when the recognition sequences are similarly predicted by the nucleotide sequence. All amino acid sequences depicted herein read from the amino terminus to the carboxyl terminus.

Group A clone nucleotide sequences and the resulting Group A immunogen amino acid sequences are exemplified by the representative clone SO67. This clone is entirely contained within the SO6 clone. Of the approximately 870 nucleotides in this clone the first 162 nucleotides starting at the 5' end have been sequenced. The transcriptional orientation and therefore the correct reading frame can be deduced unambigiously based upon the location in the nucleotide sequence of restriction enzyme recognition sequences which are predicted by restriction enzyme mapping of the CheY-SO67 recombinant plasmid. The nucleotide sequence and the resulting 53 amino acid sequence is shown in Table 6. An additional 221 nucleotide sequence, see Table 7, has been obtained from the 3' end of the clone but the reading frame has not been deduced.

Group B clone nucleotide sequences and the resulting Group B immunogen amino acid sequences are exemplified by the representative clone SO7. Clone SO7 is identical to clone SO7'. All 957 nucleotides in this clone have been sequenced. The reading frame can be deduced unambiguously by correlating the position of restriction enzyme sites asymmetrically located within the cDNA with the location of their respective recognition sequences as predicted by the nucleotide sequence analysis. The nucleotide sequence and the amino acid sequence are shown in Table 8.

Group C clone nucleotide sequences and the resulting Group C immunogen amino acid sequences are exemplified by the representative clone SP54. This clone is entirely contained within the SP59 clone. Of the approximately 700 nucleotides in this clone the first 157 nucleotides starting at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping of the CheY-SP54 recombinant plasmid. The nucleotide sequence and the resulting 52 amino acid sequence is shown in Table 9.

Group H clone nucleotide sequences and the resulting Group H immunogen amino acid sequence are exemplified by the representative clone SO311. Of the approximately 650 nucleotides in this clone, the first 185 nucleotides at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping. The nucleotide sequence and the resulting 61 amino acid sequence is shown in Table 10. The last 283 nucleotides at the 3' end have been sequenced but the reading frame has not been deduced (see Table 11).

The molecular weights of the primary translation products encoded for by the cDNAs described above are determined by in vitro translation of the appropriate mRNA populations. In vitro translation of mRNA extracted from unsporulated oocysts, sporulating oocysts and sporozoites was performed using the rabbit reticulocyte cell free translation system, with either $^{35}$S-methionine or $^{3}$H-leucine as the incorporated indicator isotope. Specific in vitro translation products were immunoprecipitated using monospecific antibodies. The protocol for in vitro translation was as described in the technical bulletin from Promega Biotec (according to manufacturer's instructions) and for immunoprecipitation as in Taylor, et al., Mol. Biochem. Parasitol. 10:305–318 (1983).

The in vitro translation product immunoprecipitated by antibody specific for the Group A antigen, exemplified by clones SO6 and SO67 has a molecular weight of about 24 kD.

The in vitro translation product immunoprecipitated by antibody specific for the Group B antigen, exemplified by clone SO7 has a molecular weight of about 28 kD while the minor immunogens have molecular weights of about 170, 24, 22, 16 and 12 kD. The additional minor specifically immunoprecipitable in vitro translation products are detectable when 3H-leucine is used as the labelled precursor amino acid. The 170 and 22 kD minor immunogens are also detectable with 35S-methionine. The major 28 kD immunogen is detectable only when 3H-leucine is used as the precursor amino acid.

The in vitro translation product immunoprecipitated by antibody specific for the Group C antigen, exemplified by clones SP54 and SP59 has not been determined.

The in vitro translation product immunoprecipitated by antibody specific for the Group H antigen, exemplified by clone SO311 has a molecular weight of about 28 kD while the minor immunogens have molecular weights of 48, 38, 33, 16, 13, 12 and 10 kD. The additional minor specifically immunoprecipitable in vitro translation products are detectable when $^{35}$S-methionine is used as the labelled precursor amino acid. The major 28 kD immunogen is detectable when both $^{35}$S-methionine and $^{3}$H-leucine are used.

The specific mRNAs extracted from sporulated oocysts and/or sporozoites of E. tenella were sized by Northern blot analysis according to the method of Maniatis, et al., Molecular Cloning, A Laboratory Manual, Cold Spring Harbor Laboratory, Cold Spring Harbor, N.Y., pg. 202 (1982) and the method described in Transfer and Immobilization of Nucleic Acids to S & S Solid supports, published by Schleicher and Schuell, Inc., pgs. 16–19 (1987).

The mRNA encoding the A immunogen, exemplified by clones SO6 and SO67, is 2.15+0.13 kilobases (kB) in length. The mRNA encoding the B immunogen, exemplified by clones SO7, is 1.23+0.22 kB in length. The mRNA encoding the C immunogen, exemplified by clones SP54 and SP59, is 1.12+0.08 kB in length. The mRNA encoding the H immunogen, exemplified by clone SO311, is 0.98+0.07 kB in length.

Native immunogens, B and C are isolated from *E. tenella* by either gel filtration and identification with specific anti-CheY immunogen antibody or immuno-affinity chromatography using specific anti-CheY immunogen antibody. *E. tenella* sporulated oocysts, about $1 \times 10^9$, are sonicated in a buffer, preferably phosphate buffered saline, containing about 0.1 mM PMSF for about 10 minutes, in about 2.5 minute bursts in an ice bath. The disrupted sporulated oocysts are collected by centrifugation at 27,000×g for 30 minutes at 4° C. The pellet is washed about 3 times with about 40 ml of PBS containing about 0.1 mM PMSF and recovered by centrifugation as described above. The washed pellet is resuspended in about 60 ml of about 5M guanidine-HCL/about 0.5M Tris-HCl, pH about 8.6, and about 400 mg DTT. Reduction was allowed to proceed for about 3 hours at 20° C. with mild agitation. Reduced and solubilized immunogen is obtained by centrifugation and collection of the supernatant fluid. The immunogen is concentrated to about 20 ml, preferably by ultrafiltration, and carboxymethylated by the addition of iodoacetic acid, about 400 mg. The pH is adjusted to about 8.6 by the addition of 3M Tris base and the reaction allowed to continue for about 60 minutes at about 20° C. in the dark. The guanidine-HCl is removed by dialysis against about 0.05M NH4HCO3, about 0.1 mM PMSF and about 0.02% sodium azide for about 48 hours. All insoluble material is removed by centrifugation. The supernatant fluid is concentrated by ultrafiltration and separated by gel filtration chromatography. The sample is applied to a column of Sephacryl S-200, about 87×2.5 cm, equilibrated in about 0.05M NH4HCO3, about 0.1% Zwittergent 3-12 and about 0.02% sodium azide. Fractions, about 4.5 ml, are collected at a flow rate of about 25 ml per hour and monitored at about 280 nm. The presence of *E. tenella* immunogen is determined by Western blotting, with rabbit anti-sporozoite antiserum and with antibody raised against the specific *E. tenella* recombinant fusion immunogens. The native immunogens are able to protect chickens against a coccidiosis infection.

Native *E. tenella* immunogens, A, B, C, H and F are isolated and purified form sporulated oocysts by immunoaffinity chromatography using antibody raised against the specific fusion immunogens. Affinity columns are prepared using preimmune serum and the specific fusion immunogen serum. Linmunoglobulin G (IgG) fractions are prepared by the method of Corthier, et al. or by the carbonyldiimidazite method of Hearn, et al. About 15 mg of IgG is coupled to 0.5 gm of Sepharose-Protein A (Sigma) using the method of Schneidert, et al. Approximately 5 mg of the reduced, carboxymethylated extract of *E. tenella* sporulated oocysts, prepared as described above, in about 0.1M borate buffer, pH 8. 1, about 0.5M NaCl, about 0.02% sodium azide, and about 0.1 mM PMSF, is applied to the prebleed column equilibrated in the same buffer. The prebleed column was washed with 3 ml of column buffer and the combined column flow-through and washes are applied to the anti-*E. tenella* fusion immunogen column equilibrated in the same buffer. The column is washed with about 10 ml of column buffer and the native immunogen is eluted with about 3M sodium thiocyanate. The individual native immunogens are able to protect chickens against a coccidiosis infection.

Immunogens from other species of Eimeria which share at least one antigen determinant or epitope are identified and isolated using antibody specific for *E. tenella* Group B immunogen. Other species which may share one or more common immunogens may include *E. acervulina, E. mivati, E. mitis, E. praecox, E. hagani, E. necatrix, E. maxima* and *E. bumetti*. The antibody is prepared as described above and may be either polyclonal or monoclonal. Immunogens used to produce the antibody include native Group B immunogen or recombinant proteins expressed from any of the Group B clones, with the SO7 clone immunogen being preferred. The recombinant immunogens may be either the individual protein or a fusion protein, with the SO7-CheY fusion protein immunogen being preferred.

Immunogens associated with the various Eimeria species which share one or more epitopes with Group B *E. tenella* immunogen are identified by immunoblotting of immunogens prepared from sporulated oocysts and sporozoites of each individual species. The sporulated oocysts and sporozoites are physically disrupted, the proteins separated by SDS-polyacrylamide gradient gel electorphoresis and transferred to nitrocellulose. The transferred proteins are reacted with the anti-SO7-CheY antibody and bound antibody is detected with 125I-protein A.

Native Group B immunogens are isolated from Eimeria species sporulated oocysts by sonication, reduction and carboxymethylation. The reduced and carboxymethylated proteins may be pre-purified by size exclusion chromatography. Immunoaffinity matrices containing anti-Group B antibody are prepared using the technique of Bethel, et al., J. Biol. Chem., 254:2572–2574(1979) as described above. The Group B immunogens isolated from Eimeria species other than *E. tenella* are able to protect chickens against a coccidiosis infection.

Molecular weights and isoelectric points of Eimeria immunogens are also determined. Molecular weights are determined by analytical sodium dodecyl sulfate (SDS) polyacrylamide gel electrophoresis (PAGE) of samples prepared from sporulated oocysts and/or sporozoites of *E. tenella*, followed by transfer to nitrocellulose and immunodetection by Western Blotting as described above. Appropriate molecular weight controls are included. Isoelectric points were determined by Western Blotting of two dimensional gels run according to the procedure of O'Farrell, J. Biol. Chem. 250:4007–4021 (1975). Antibodies for both procedures are prepared as stated above. Imunogen A separated as a single band with a molecular weight of 24 kiloDaltons (kD). The predominant B immunogen is characterized as a diffuse doublet of 27–28 kD on SDS-PAGE with the minor immunogens appearing as faint bands suggesting some sharing of antigenic determinants within *E. tenella*. The minor bands have molecular weights of 22, 19, 18, 14, 12, 9, and 6 kD. The 27–28 doublet produces multiple spots on isoelectric focusing, in the range between pH 5.1 and 6 kD. The pIs of the faint additional bands detected by Western blotting were not determined. Immunogen C also migrates as a doublet with molecular weights of 21–22 kD. Immunogen H separates as two distinct major proteins with molecular weights of 28 and 18 kD and seven minor proteins with molecular weights of 27, 24, 23, 17, 14, 12, and 9 kDs. The Group F immunogen has a molecular weight of about 26–29 kD. The isoelectric points of immunogens A is 3.65 and H is 6.65. The isoelectric points of C and F have not been determined.

Poultry are administered an immunizing dosage of one or more of the recombinant derived *E. tenella* immunogens described above. Immunogen administration to chickens may be by oral or parenteral routes or chicken embryos may be inoculated through the egg shell. Administration of immunogen by any of these routes may include an immunogen or immunogens given alone or as a solution or suspension with a physiologically acceptable medium. Such physiologically acceptable media include, but are not limited to, physiological saline, phosphate buffered saline, phosphate buffered saline glucose, buffered saline and the like. Parenteral administration includes inter alia, intramuscular, intraperitoneal, subcutaneous and intravenous injection or delivery of the *E. tenella* immunogens. Orally administered immunogens can be in the form of an aqueous solution or suspension. A suspension may include the immunogen in a gel composed of, for example, gelatins or alginates. Orally administered immunogens may also be included in the feed. Embryonated eggs are immunized by the injection of an immunogenic dose of one or more of the Eimeria immunogens. The immunogens for intramuscular and subcutaneous vaccination may be given along with an acceptable adjuvant. Acceptable adjuvants include, but are not limited to, Freund's complete, Freund's incomplete, double emulsions, anhydrous oils, alum-precipitate, water-in-oil emulsion containing *Corynebacterium parvum* and t-RNA. The preferred adjuvant is alum-precipitate, in which the immunogen has been precipitated with aluminum hydroxide such as Alhydrogel™. Immunization of chickens with recombinant derived *E. tenella* immunogens results in immunity to coccidiosis. Protective immunity is achieved by administration of from about 1.0 ng to about 100 $\mu$g, with about 100 ng to about 10 $\mu$g being preferred.

The following examples illustrate the present invention without, however, limiting the same thereto.

EXAMPLE 1

Preparation of Oocysts, Sporulated Oocysts, Sporozoites and Schizonts and the Corresponding Immunogens and Antigens

*E. tenella* oocysts were isolated from cecal cores (coalesced masses of oocysts) from chickens infected 7 days earlier.

*E. acervulina* oocysts were isolated from feces and intestinal contents of chickens infected 5 to 6 days earlier.

The isolated cecal cores and feces were separately disrupted in a Waring Blender (in distilled water), digested with pepsin (2 mg/ml) at pH 2.0 at 39° C. for 1 hour. Large amounts of debris and the pepsin were removed from pelleted material after centrifugation (1,000×g) in distilled water. A partially pure oocyst fraction was isolated from the pellet by flotation in 2.2M sucrose (Jackson, Parasitol, 54: 87–93, 1964), and this crude material was further treated by incubating in cold Clorox (5.25% sodium hypochlorite, at 4° C.) for 10 minutes. The sodium hypochlorite was removed by several washes in sterile phosphate-buffered saline (PBS) pH 7.6 to obtain purified and sterile oocysts. Oocysts were sporulated in a shaking water bath at 20° C. for 48 hours (Edgar, Trans. Am. Micr. Soc. 62: 237–242, 1954). Sporulated oocysts were stored in PBS (pH 7.6) at 4° C.

Fully sporulated oocysts were sonicated on ice in a Bransonic cell disrupter, with a tapered probe. Sonication was performed using a 30 second on/off cycle to prevent overheating. Following this procedure, 90% breakage was achieved within 10–15 minutes. Detergent (Zwittergent 3-12, Calbiochem, 0.1% w/v) was added, and the mixture was stirred at 4° C. for 18 hours. After centrifugation at 27,000×g for 30 minutes, the supernatant was subjected to gel permeation chromatography on Sephadex S-200 (Pharmacia).

A column of Sephadex S-200 (8×44 cm) was equilibrated at 4° C. with 50 mM $Na_2HPO_4$—$NaH_2PO_4$, pH 7.2 and 0.1% Zwittergent 3-12. The sonicate was applied to the column, eluted with the same buffer and fractions collected (14 ml) and monitored by absorbance at 230 nm. Fractions were pooled according to the SDS-PAGE profile. Pooled fractions were dialysed against eight liters of 10 mM ammonium bicarbonate at 4° C. for one week with three changes of buffer, and were then freeze-dried. The lyophilized fractions were dissolved in glass-distilled water and were tested for in vivo activity, chicken protection. In vivo activity was routinely found between fractions 84–94. The protective *E. tenella* fractions were pooled and designated Fraction V. For some batches, S-200 chromatography was performed in 50 mM ammonium bicarbonate, pH 7.7, containing 0.05% Zwittergent. This had no effect on the elution profile or on the in vivo efficacy.

Second generation schizonts were prepared from chicken intestinal cells four days post-infection according to the protocol of James, Parasitol, 80: 301–312 (1980).

Immunogens for antibody production were prepared as follows. A 2 ml suspension of purified sporulated oocysts ($5\times10^7$ per ml PBS, pH 7.6) was ground at 500 rpm for 5 minutes at 4° C. in a tissue homogenizer with a loose-fitting pestle (Patton, Science 150: 767–760, 1965) and the supernatant fluid resulting from the disruption of the oocysts was removed after centrifugation (600×g for 10 minutes). The *E. tenella* pellet, composed of unbroken oocysts, sporocysts, and oocyst shells, was resuspended in an excysting solution containing 0.25% (w/v) trypsin (1:250) and 4.0% (w/v) taurodeoxycholic acid (Sigma) in Hanks balanced salt solution (pH 7.4) and incubated at 41° C. in 5% $CO_2$ (Patton et al, J. Parasitol. 65: 526–530, 1979). The *E. acervulina* pellet, also composed of unbroken oocysts, sporocysts and oocyst shells, was resuspended in an excysting solution containing 0.125% (w/v) trypsin (1:250) and 1.0% taurodeoxycholic acid in Hank's Balanced salt solution (pH 7.4) the pellets were incubated at 41° C. in an atmosphere containing 5% $CO_2$. Excystation was allowed to continue for ½ hour for *E. acervulina* and 1 hour for *E. tenella* after which the excysting solution was removed by centrifugation and parasite material was washed twice in phosphate buffered saline/glucose (PBSG) buffer of pH 8.0, ionic strength 0.145 containing 1% glucose, Schmatz, et al., J. Protozool. 31:181–183, 1984. The parasite mixture was applied to a DE52 anion exchange column, equilibrated in PBSG, and purified sporozoites were eluted unretarded in the void volume (Schmatz, et al., supra).

Sporozoites were freeze-thawed 3 times (dry ice to room temperature and sonicated until disrupted in PBS with 1 mM PMSF as protease inhibitor to provide sporozoite antigen. Protein concentrations were determined by the method of Lowry, et al., J. Biol. Chem. 193: 265–275, 1951 and antigens were stored in liquid $N_2$.

EXAMPLE 2

Production of Anti-*Eimeria tenella* Unsporulated Oocyst, Sporulated Oocyst, Sporozoite, Schizont, Anti-Fraction V and Anti-*E. acervulina* Sporozoite Antibodies Rabbits (New Zealand White, female) were multiply immunized with one of the various immunogens described in Example 1. Each immunization dose contained 50 μg of protein. The first immunization was given in Friend's complete adjuvant. Subsequent immunizations were given in Friend's incomplete adjuvant. The antigen adjuvant mixture was prepared by emulsifying 0.5 ml of antigen containing 50 μg protein in PBS with 0.5 ml of adjuvant. One ml of emulsion was then administered subcutaneously in multiple sites on a shaved area of the rabbit back. Secondary booster immunizations were given at approximately one month intervals following primary immunization. Animals were bled and immune sera prepared at approximately monthly intervals, starting six weeks after the start of the immunization schedule. Immune activity and specificity was determined by Western blot analysis using the specific extract antigens from Example 1 and the technique of Towbin, et al., Proc. Natl. Acad. Sci. U.S.A. 76:4350–4354 (1979). Each antibody was specific for its corresponding immunogen, antigen.

EXAMPLE 3

Immunization of Two-Day-Old Chickens Against Coccidiosis with Fraction V Immunogens Broiler chicks were immunized with Fraction V immunogen as described in Example 1. The dosage was based on protein content as determined by the method of Lowry, et al., J. Biol. Chem. 193: 265–275 (1951) and was given intramuscularly on days 2, 9 and 16 following hatching. Experimental and control chickens were challenged one week after the last immunization with an oral inoculation of $5 \times 10^3$ E. tenella oocysts. Six days after challenge the chickens were killed and the severity of the lesions in the ceca were determined according to the method of Johnson and Reid, Exp. Parasitol. 28: 30–36 (1970).

The following results were obtained.

TABLE 4

| Immunogen | Dose (mg) | Number of Birds | Mean Group Lesion Score |
| --- | --- | --- | --- |
| Fraction V | 10.0 | 8 | 1.0 |
| Fraction V | 1.0 | 8 | 1.6 |
| Fraction V | 0.10 | 8 | 2.9 |
| None | — | 8 | 3.4 |

These results show that Fraction V immunogen can be used to immunize two-day-old chickens. An intramuscular inoculation provides a high level of protection against the disease as indicated by the absence of severe lesion development in immune birds after a normally virulent infection.

EXAMPLE 4

Preparation of Genomic DNA from E. tenella Sporozoites

Purified E. tenella sporozoites, from Example 1 were suspended in TE medium (10 mM Tris-HCl, pH 7.5, 0.1 mM EDTA) at a concentration of $1.5 \times 10^8$ sporozoites per ml. The dilute suspension of sporozoites was then adjusted to 0.5% in SDS (from a 20% SDS stock solution), and 15 mM in EDTA (from a 0.5M-pH 8.0 stock solution) which resulted in both plasma and nuclear membrane lysis. The release of genomic DNA following nuclear lysis is marked by an obvious increase in the viscosity of the solution. To aid in solubilization, the solution was gently rocked at 50° C. on a platform for 30–60 minutes, and then digested for 3 hours at 50° C. with Proteinase K at a concentration of 100 ug per ml. Genomic DNA was purified by two extractions with phenol, two extractions with a mixture of phenol, chloroform and isoamyl alcohol (25:24:1), two extractions with chloroform and isoamyl alcohol (24:1), and two successive precipitations with sodium acetate/ethanol as described in Example 8. The nucleic acid pellet was washed twice with 70% ethanol and suspended in TE at an approximate concentration of $5 \times 10^8$ sporozoite equivalents per ml. The RNA component of the nucleic acid was selectively removed by digestion with heat inactivated RNase A at a concentration of 50 ug per ml for 60 minutes at 37° C. The RNase A and other residual proteins were removed by a secondary digestion with Proteinase K in 0.5% SDS and 15 mM EDTA for 3 hours at 50° C. as described above. Genomic DNA was then successively extracted with organic solvents, precipitated twice with ethanol, and then washed twice with 70% ethanol. The genomic DNA pellet was suspended in TE at a concentration of $2-3 \times 10^9$ sporozoite equivalents per ml and quantitated by absorbance at 260 nm. Undigested genomic DNA was then fractionated on an analytical gel to confirm (i) the spectrophotometrically-derived concentration, (ii) the lack of residual RNA, and (iii) its high molecular weight integrity.

EXAMPLE 5

Construction of cDNA Expression Libraries

E. tenella oocysts, sporulated for seven hours, and sporozoites were prepared as previously described (Schmatz et al, supra; Wang & Stotish, J. Protozool. 22: 438–448, 1975). Total RNA was isolated from each stage either immediately after isolation (i.e., the sporozoites) or from cell pellets frozen in liquid nitrogen and stored at –80° C. (i.e., the 7 hour sporulating oocysts) by the method of Chirgwin, et al., (Biochem. 18: 5294–5299, 1979). Due to the presence of the cell wall, oocyst samples were resuspended in 4 volumes of 4M guanidinium thiocyanate solution (volumes of solution relative to volume of cell pellet) and were sonicated for a total of 30 minutes at 20 W, 50% cycle with a Branson sonifier (Heat System Ultrasonics). Sporozoites were lysed upon the addition of the guanidinium thiocyanate stock solution (4M guanidinium thiocyanate, 0.5% N-lauroylsarcosine, 25 mM sodium citrate, pH 7.0, and 0.1M 2-mercaptoethanol); therefore sonication was unnecessary. The lysed cells were then centrifuged at 9,000 rpm for 10 minutes in a Beckmann JS-13 rotor at 10° C. to sediment particulate cellular debris. The supernatants were decanted into a clean flask and mixed with 0.025 volumes of 1M acetic acid and 0.75 volumes of absolute ethanol. The flask was shaken thoroughly and left to stand overnight at –20° C. to precipitate the nucleic acids. The next day, the RNA was collected by centrifugation in a Beckmann JS-13 rotor at 8000 rpm for 10 minutes at 10° C. The tubes were drained and the cell pellet was resuspended in 0.5 volumes of buffered guanidine hydrochloride stock solution (7.5M guanidine hydrochloride, 0.025M sodium citrate, pH 7.0, and 5 mM DTT). The volume of the guanidine hydrochloride stock solution is relative to the volume of the guanidinium thiocyanate solution previously used. The RNA was precipitated by adding 0.025 volumes of 1M acetic acid and 0.5 volumes of absolute ethanol. The solution was kept overnight at –20° C. and the RNA was collected once again by centrifugation. The guanidine hydrochloride precipitation was repeated, using half the volume of the guanidine hydrochloride stock solution used in the previous precipitation. The reprecipitated RNA was washed in 95% ethanol, dried, and resuspended in sterile water. This material was centrifuged for 30 minutes at 10,000 rpm (Beckmann JS-13 rotor) at 10° C. The supernatant fluids were saved and the pellets were resuspended in sterile water. The centrifugation step was repeated. The supernatant fluids were combined, mixed with 0.1 volume of 2M potassium acetate, pH 5, and 2 volumes of absolute ethanol, and were left to precipitate overnight at −20° C. The RNA pellets were collected by centrifugation at 10,000 rpm (Beckmann JS-13 rotor) for 30 minutes, dried, and resuspended in sterile water. The concentration of the RNA was determined by spectrophotometry.

Polyadenylated RNA was selected by oligo (dT)-cellulose chromatography (Aviv & Leder, Proc. Nat. Acad. Sci. U.S.A. 69: 1408–1412, 1972). To make a 1 ml column, 0.3 g of oligo (dT)-cellulose (Bethesda Research Laboratories, BRL) was resuspended in elution buffer (10 mM Tris-HCl, pH 7.5) and poured into a Pasteur pipette. Before use, the column was washed with 10 bed volumes of binding buffer (0.5M lithium chloride, 0.5% sodium dodecyl sulfate, 10 mM Tris-HCl, pH 7.5, and 1 mM ethylenediamine tetraacetic acid).

The RNA (0.5 mg), dissolved in sterile water, was heated at 68° C. for 5 minutes and cooled to room temperature on ice. An equal volume of 2× binding buffer was added, mixed thoroughly, and the sample was applied to the column. After washing the column with 50 mls of binding buffer, the poly(A+)-RNA was eluted with 10 mls of elution buffer. Ten, 1 ml fractions were collected and the concentration of RNA in each was determined by spectrophotometry at a wavelength of 260 nM. The fractions with the highest absorbance were pooled and RNA was precipitated by adding 0.1 volumes of 2M potassium acetate, pH 5.0, and 2 volumes of absolute ethanol. The samples were left overnight at −20° C. and the RNA was collected by centrifugation as above. After precipitation, the samples were resuspended in sterile water and the concentration of each was redetermined by spectrophotometry.

Starting with 7.5 μg of poly(A+)-RNA, first and second strand cDNA reactions were performed as described by Gubler and Hoffman (Gene 25:263–269, 1983). Synthesis of the first strand of the cDNA was carried out in a reaction volume of 40 ml containing 50 mM Tris-HCl, pH 8.3, 10 mM $MgCl_2$, 10 mM DTT, 4 mM Na-pyrophosphate, 1.25 mM dGTP, 1.25 mM dATP, 1.25 mM TTP, 0.5 mM dCTP, 15 μCi of [a-$^{32}$P] dCTP (3000 Ci/mmol), 100 μg/ml of oligo (dT12-18), 3000 units AMV reverse transcriptase/ml (Beard, Life Sciences, St. Petersburg, Fla.) for 30 minutes at 42° C. The products were extracted with phenol/chloroform and precipitated with absolute ethanol out of 2M NH4-acetate, Okayama & Berg, Mol. Cell Biol. 2: 161–170, 1982. The pellets were washed with 70% ethanol, dried, and resuspended in 40 ml of sterile water.

For second strand synthesis, 500 ng of single-stranded cDNA (i.e. 1 mg of the cDNA/mRNA hybrid) was resuspended in 100 ml of 20 mM TRIS-HCl, pH 7.5, 5 mM MgCl2, 10 mM $(NH_4)2SO_4$, 100 mM KCl, 0.15 mM β-NAD, 50 μg per ml BSA, 40 mM each of dATP, dGTP, dCTP and dTTP, 8.5 units/ml of *E. coli* RNase H (Pharmacia P-L 30 Biochemicals, Inc.) and 230 units per ml *E. coli* DNA polymerase I (Pharmacia P-L Biochemicals, Inc.). Incubations were sequentially carried out at 12° C. for 60 minutes and at 22° C. for 60 minutes. EDTA was added to 20 mM to stop the reaction and the products were extracted twice with phenol/chloroform. The double stranded cDNA was precipitated with 2 volumes of absolute ethanol from 2M $NH_4$-acetate as previously described.

The cDNA (500 ng-1 mg) was then methylated in a 20 μl volume of 1× EcoRI methylase buffer containing 50 mM Tris-HCl, pH 7.5, 1 mM EDTA, 5 mM DTT, and 10 μM S-adenosylmethionine. The reaction was carried out at 20° C. for 20 minutes after the addition of 20 U of EcoRI methylase (New England Biolabs). To terminate the reaction, the enzyme was heat inactivated for 15 minutes at 70° C. The samples were cooled on ice and the cDNA was blunt-ended as follows. To the tube containing 21 μl of EcoRI-methylated cDNA, 2.5 μl of 0.1M MgCl2, 2.5 μl of 0.2 mM d (A, C, G, T) TP and 5 units of T4 DNA polymerase (BRL) were added. The reaction was carried out at 20°–22° C. for 10 minutes and terminated with the addition of EDTA to a final concentration of 15 mM. The reaction products were extracted twice with phenol/chloroform and precipitated with ethanol as above.

The pellets from the previous reactions were resuspended in 4.5 ml of 100 mg/ml kinased EcoRI dexanucleotide linkers (BRL) in buffer containing 70 mM Tris-HCl, pH 7.6, 10 mM MgCl2, 5 mM DTT, and 1 mM ATP. T4 DNA ligase (New England Biolabs, 200 U/0.5 ml) was added and the reaction mixture was incubated overnight at 12° C. The linker ligated cDNA's were then digested to completion with EcoRI (BRL). To the 5.5 ml overnight incubation, 5 ml of EcoRI correcting buffer (50 mM Tris-HCl, pH 7.5, 10 mM $MgSO_4$, 200 mM NaCl) was added. The mixture was heated for 10 minutes at 70° C. to inactivate the ligase. The volume of the reaction mixture was increased two-fold (to 20 μl) with 100 mM Tris-HCl, pH 7.5, 50 mM NaCl, and 10 mM $MgCl_2$ and 2 μl of EcoRI restriction endonuclease (16 units/ul) was added. The digest was allowed to proceed for one hour at 37° C. after which the enzyme was heat inactivated for 20 minutes at 65° C. The products were precipitated as above.

To remove the digested linkers from the reaction mixture, the cDNA was further purified on an Elutip-d column (Schleicher and Schuell). Finally, the cDNA (300 ng) was ligated into 7.5 μg of commercially purchased EcoRI-digested, alkaline phosphatase treated ggt11 vector DNA (Promega Biotec). The vector-to-donor molar ratio in the ligation mixture was 1:1, and the final concentration of DNA was approximately 200 μg/ml. The ligation reaction was carried out in 10 mM Tris-HCl, pH 7.5, 10 mM MgCl2. To anneal the cohesive ends of the gt11 vector, the mixture was first incubated at 42° C. for 15 minutes. It was then supplemented with 1 mM ATP, 10 mM DTT, and 40,000 units/ml of T4 DNA ligase (New England Biolabs). The reaction was incubated overnight at 14° C.

The λ vector hybrids were packaged in vitro with commercially available packaging extracts according to the manufacturer's instruction (Amersham). Small aliquots of the packaged phage were transduced into *Escherichia coli* host strain Y1088 (Huynh, et al., In "DNA cloning: A practical approach", Volume I, Glover, D. ed., IRL Press, Oxford, pp 49–78, 1985) and these were plated on LB plates using 2.5 ml of LB (10 g per L Bactotryptone, 5 g per L Bacto-yeast extract, 10 g per L NaCl, pH 7.5) soft agar containing 600 μg ml-1 X-gal and 16 mM IPTG. Two cDNA libraries, each consisting of approximately 1×10$^7$ independent recombinant phage clones were generated. The nonrecombinant background, as determined by growth on X-gal/IPTG plates, was estimated to be 13%.

EXAMPLE 6

Screening of λt11 cDNA Libraries

The screening of the cDNA libraries from Example 5 with either anti-Fraction V antibody or anti-sporozoite antibody, from Example 2, was done essentially as described by Huynh, et al., supra. Packaged phage from the unamplified cDNA library were transduced into *E. coli* strain Y1090 and plated on 150 mm plates at a density of 0.5–1.0×10$^5$ plaque forming units (pfu) per plate. The plates were incubated at 42° C. for 3.5 hours, overlaid with dry nitrocellulose filters presoaked in 10 mM IPTG, and incubated overnight at 37° C. The filters were removed, blocked for 1 hour with 20% fetal calf serum in Tris buffered saline (TBS; 50 mM Tris-HCl/150 mM NaCl, pH 9.0) containing 0.05% Tween 20 (TBST), and were then incubated with the appropriate antibody for an equivalent length of time. Antibody binding sites were detected with [$^{125}$I] labeled protein A. Positive plaques were picked, replated, and rescreened until each clone was shown to be plaque pure.

For cross-screening experiments, 1 μl of phage lysate from each plaque purified clone was spotted on a lawn of *E. coli* Y1090 cells. Recombinant fusion proteins were induced, transferred to nitro-cellulose, and immunoblotted as described below. Screening and cross-screening with the various antisera revealed the five groups of clones in Table 1. All of the antisera used for immunoblotting were exhaustively preabsorbed with a concentrated lysate of λgt11 lysogen BNN93. After preabsorption, they were diluted 1:100 in TBST and stored at 4° C. until required.

Monospecific antibodies to each of the recombinant phage were affinity purified from poly-specific antisera, from Example 2, by a modification of the method of Hall, et al. (Nature 311: 379–382, 1984) and by immunizing rabbits as described in Example 2 with the purified recombinant *E. tenella*-CheY fusion proteins as described in Example 13. The fusion proteins included Group A, SO67-CheY; Group B, SO7-CheY, Group C, SP54-CheY; Group H, SO311-CheY; and Group F, SO216-CheY. Filter plaque lifts were prepared from purified recombinant clones as was done for screening. Approximately 2×10$^5$ pfu were plated per 150 mm plate to give close to semiconfluent lysis at the end of the 37° incubation period. The nitrocellulose was then removed, blocked with 20% fetal calf serum in TBST for 4 hours, and incubated overnight with 20 ml of preabsorbed polyspecific serum (diluted 1:200 with 20% fetal calf serum in TBST containing 0.02% NaN3). All of the incubations were done at room temperature with constant agitation. Subsequently, the filters were washed five times for 20 minutes each with 50 ml of TBST and one time with 0.15M NaCl/0.05% Tween 20. The antibodies were eluted from each of the filters with 10 ml of 0.2M glycine-HCl/0.15M, NaCl/0.05% Tween 20, pH 2.8 for 30 minutes. The pH of each eluate was restored to 8.0 with Tris base and the recombinant eluted antibodies (REA's) were stored at −20° C. until required.

Parasite antigens were obtained by sonicating unsporulated oocysts, sporulated oocysts, and DE-52 purified sporozoites in NET buffer (50 mM Tris-HCl, pH 7.5, 150 mM NaCl, 5 mM EDTA) with 1 mM PMSF as a protease inhibitor as described in Example 1. Protein concentrations of each sample were determined by method of Lowry, et al., supra. The yield of antigen from 3×10$^5$ unsporulated/sporulated oocysts was approximately 50 μg, whereas the same amount of antigen was obtained from approximately 2×10$^6$ sporozoites. Samples were kept at −20° C. until ready for use. For blots of parasite antigens, 50 μg of each sonicated sample was mixed with an equal volume of 2× sample buffer (0.125 Tris-HCl, pH 6.8, 4% w/v SDS, 10% v/v 2-mercaptoethanol, 20% glycerol and 0.0025% bromophenol blue), boiled for 3 minutes and electrophoresed on either a 15% SDS-polyacrylamide gel or a 5–20% SDS-polyacryl-amide gradient gel (Laemmli, Nature 227:680–684, 1970).

Alternatively antigens were prepared by resuspending oocysts at a concentration of 5×10$^7$ per ml and sporozoites at a concentration of 5×108 per ml in NET buffer containing a cocktail of protease inhibitors (2 mg ml-1 1–10 phenanthroline, 2 mg ml-1 benzamidine, 0.002 mg ml-1 PMSF, 0.048 mg ml-1 Sigma soybean trypsin inhibitor, 0.048 mg ml-1 aprotinin, 0.02 mg ml-1 leupeptin). At this point the samples were mixed with an equal volume of 2× sample buffer without bromophenol blue. The samples were boiled for 3 minutes, sonicated till fully disrupted, and reboiled again for 3 minutes. Bromophenol blue was added to 0.0025% and the samples were stored at −20° C. until ready for use. For immunoblotting, oocyst or sporozoite antigens were loaded and subjected to electrophoresis as stated above.

Proteins separated by SDS-PAGE were electrophoretically transferred to nitrocellulose by the technique of Towbin, et al., Proc. Natl. Acad. Sci. U.S.A., 76:4350–4354 (1979). The nitrocellulose was subsequently blocked with 20% fetal calf serum in TBST for 4 hours. After blocking, the nitrocellulose was incubated overnight at room temperature in 20 ml of antibody diluted with 20% fetal calf serum in TBST containing 0.02% NaN3. Polyspecific antisera were diluted 1:100 to 1:200 and monospecific recombinant eluted antisera were diluted 1:10. Following the contacting with specific antibody, the filters were washed three times for 5 minutes each with 200 ml of TBST. Bound antibody was detected with $^{125}$I-protein A diluted in 20 ml of TBST to a final concentration of 2×10$^5$ counts per minute ml-1. Incubation with radio-labelled protein A was carried out for 1 hour at room temperature after which time the filters were again washed three times for 5 minutes with 200 ml of TBST, were air dried, and exposed to Kodak X-omat AR film.

Alternatively, the nitrocellulose was blocked with 0.5% gelatin in phosphate buffered saline, pH 7.4, for 1 hour with three 200 ml washes followed by a second blocking with 0.25% gelatin in TEN buffer, 50 mM Tris-HCl, 150 mM NaCl, 5 mM EDTA, pH 7.4, for 1 hour and washed as before. After blocking, the nitrocellulose was incubated overnight at room temperature in 20 ml of antibody diluted 1:100 to 1:200 with TEN buffer containing 0.25% gelatin and 0.05% Triton X-100. The filters were washed 5 times for 20 minutes each with 200 ml of TEN containing 0.25% gelatin. Bound antibody was detected with 125I-protein A diluted in 20 ml of TEN, 0.25% gelatin, 0.05% Triton to a final concentration of 2×105 cpm ml-1. Incubation with radiolabelled protein A was carried out for 1 hour at room temperature, after which time the filters were washed 2 times for 15 minutes with 200 ml of TEN containing 0.25% gelatin and 0.05% Triton and 4 times for 15 minutes with 200 ml of TEN. After washing, the filters were air dried and exposed to Kodak X-omat AR film.

EXAMPLE 7

Preparation of phage DNA

Recombinant and wild type λgt11 phage from Example 6, were introduced as lysogens into *E. coli* host strain Y1089 (Huynh, et al., supra) at a multiplicity of 10. The lysogens were streaked on to LB-plates containing 100 μg ml-1 ampicillin for single colony isolation and incubated overnight at 30°–32° C. The growth of several colonies was checked at 32° C. and 42° C. One colony was picked from a 32° C. plate that did not grow at 42° C., and an overnight culture was set up in LB broth with 50 μg L-1 ampicillin.

The lysogenized clones were then grown from the overnight culture in 50 ml of LB broth containing 50 μg ml-1 ampicillin at 32° C. until an O.D. 600 of 0.3 to 0.5 was reached. Phage excision and replication was induced by a temperature shift to 45° C. for 20 minutes. Continued phage replication was insured by continuing to grow the cultures at 37° C. for 2 to 3 hours, until sign of cell lysis was visible. If the cultures were not completely lysed, 0.1 ml of chloroform was added to each, and the cultures were agitated for an additional 10 minutes at 37° C. Under these conditions, lysis of the cells occurs after a few minutes. The cellular debris was routinely removed, at this point, by centrifugation for 5 minutes at 7,000 rpm in a Beckmann JS-13 rotor. The phage supernatant fluids were stored overnight at 4° C. after adding $MgSO_4$ to a final concentration of 0.01M, to stabilize the phage heads.

After bringing the phage supernatant fluids to room temperature, 50 μl of 10 mg ml-1 DNase I and 25 μl of 10 mg ml-1 RNase A were added to each sample. These were incubated for minimally one hour at 30° C., after which 1.46 g of NaCl was added and thoroughly dissolved in each. The supernatant fluids were incubated further on ice for a minimal time of 30 minutes. The remaining cellular debris was then collected by centrifugation for 10 minutes at 10,000 rpm in a Beckmann JS-13 rotor. The supernatants were collected from each sample and in each supernatant fluid, 3.5 gm of Carbowax PEG 8000 (polyethyleneglycol 2000, Fisher Scientific Co.) was dissolved. In the presence of PEG, the phage heads were left to precipitate overnight at 4° C. The next day, the phage heads were collected by centrifugation. The supernatant fluids were centrifuged for 10 minutes at 10,000 rpm in a Beckmann JS- 13 rotor maintained at 4° C. The supernatant fluids were carefully drained off and discarded. The pellets were resuspended in 250 μl of 0.1M Tris-HCl (pH 7.9), 0.3M NaCl, and 1 mM EDTA, after which 12.5 μl of 0.5M EDTA was added to chelate any free $Mg^{++}$ left behind in the sample. The phage heads were incubated in the aforementioned buffer for 10 minutes at 67° C. After the incubation, 5 μl of 10% SDS was added to each sample and the samples were mixed on a vortex mixer. Heating was used to denature the phage proteins. The SDS completes the denaturation step, and releases the DNA from the phage heads.

The DNA which has been released from the phage is then extracted twice with phenol, three times with chloroform-isoamyl alcohol (24:1), and precipitated with the addition of one-tenth volume of 3M NaOAc (pH 7.5) and two volumes of absolute ethanol. The samples were left to precipitate overnight at -20° C. The next day, the DNA was collected by centrifugation in a microfuge for 20 minutes. The precipitated DNA was redissolved in 300 μl of 0.3M KOAc and reprecipitated with the addition of two volumes of absolute ethanol. The samples were incubated at -80° C. for 10 minutes and the DNA was collected by centrifugation as described above. The DNA pellets were washed with 70% ethanol, dried, and resuspended in 100 μl of TE buffer (10 mM Tris-HCl (pH 7.6), 1 mM EDTA (pH 8.0). The concentration of DNA in each sample was determined by spectrophotometry at a wavelength of 260 nM.

EXAMPLE 8

Purification of cDNA Insert From λ-gt11 Clones

Ten to 20 μg of λ-gt11 recombinant phage, from Example 7, (at a final DNA concentration of 0.2 μg/ul) was cut to completion with EcoRI (80U/ml; Boehringer Mannheim) in a reaction buffer composed of 50 mM NaCl/100 mM Tris-HCl (pH 7.5)/5 mM $MgCl_2$. The reaction was conducted at 37° C. for 4 hours using a 5-fold enzyme excess. Reaction products were adjusted to 0.3M sodium acetate by the addition of one-tenth volume of a 3M (pH 5.6) stock solution, precipitated with 2.5 volumes of ethanol, chilled for 20 minutes at -70° C., and collected by centrifugation at 15,000×g for 15 minutes at 4° C. The pellet was suspended in 30 μl of TE (10 mM Tris-HCl, pH 7.5/0.1 mM EDTA) and loaded onto a preparative 1% agarose flat bed gel containing ethidium bromide. The insert was resolved from the phage arms by electrophoresis overnight (15 hr/60 mA).

Fractionation of the insert was verified by visualization under ultraviolet light. The agarose gel was sliced on both sides of the cDNA insert and pieces of NA-45 membrane (Schleicher & Schuell) were inserted into the gel, "sandwiching" the cDNA insert. The insert was then electrophoresed onto the NA-45 membrane. Upon completion, the membrane was removed from the gel, cut into small pieces and placed into an Eppendorf tube with 250 ml of a solution composed of 50 mM arginine (free base), 1M NaCl. DNA was eluted from the membrane at 70° C. for 3 hr; the aqueous solution was removed and the elution process was repeated using a fresh 250 μl of eluant. The two eluates (totaling 500 μl) were combined and chilled to 4° C. Insoluble particulates were collected by centrifugation for 10 minutes at 4° C. at 15,000×g. The soluble material was then extracted twice with phenol, twice with phenol/chloroform/isoamyl alcohol (25:24:1) and twice with chloroform/isoamyl alcohol (24:1). DNA was precipitated with 0.3M sodium acetate/EtOH (as described above), washed twice with 70% EtOH, air dried, suspended in 25 μl of TE and quantitated by absorbance at 260 nM. An aliquot of the DNA was then analyzed on an analytical agarose gel for confirmation.

EXAMPLE 9

Mapping of cDNA clones isolated from ggt11 library

DNA inserts, from Example 8, were isolated from phage clones representative of Group A (SO6', SP1, SO67), Group B (SO9, SO24, SO7', SO1'), Group C (SP54, SP59) Group H (SO311, SO227, SO231) and Group F (SO216). The phage inserts were subcloned into the plasmid vector, puc18, which is commercially available from Bethesda Research Lab. Both the isolation of inserts as well as the subcloning were done as described for the CheY vector, pJC264 in Example 12. The plasmids were grown as mini-preparations in 5 ml cultures of LB broth, and the DNA was isolated from each, using the alkaline lysis method as described in Example 12. The DNA was resuspended in 50 μl of TE buffer, 10 mM Tris-HCl (pH 8.0), 1 mM EDTA (pH 8.0), containing DNase-free pancreatic RNase (20 μg ml-1) and by brief vortex mixing. The DNA samples were then digested with a variety of restriction endonucleases (commercially available from many suppliers including Bethesda Research Laboratories) in order to determine which were cutters or noncutters of the cDNA inserts. The restriction enzyme digestions were always done according to the manufacturer's recommendations. Usually five cutters were chosen for each clone, and a mapping analysis was conducted by doing single and double digests of each recombinant plasmid. The DNA fragments which were generated were separated electrophoretically on 1% agarose gels, and sized by comparison to DNA markers which were run simultaneously on the same gels. Maps were constructed of each clone by entering the fragment size data and known vector restriction sites into the Intelligenetics Restriction Map Generator program (MAP Intelligenetics, Inc.). In each case, the map which is the most compatible with all of the data is shown in the FIGS. I–V.

EXAMPLE 10

Construction Of The CheY-ANF Plasmid

An expression plasmid for the fusion polypeptide SC1N-(rat-ANF-26) was derived from the pSCN1 plasmid. The pSCN1 plasmid is a bacterial-expression plasmid for the N-terminal 165 amino acids of the yeast RAS1 protein SC1N and is described in Temeles, et al., Nature 313: 700–703 (1985). The plasmid pSC1N (1 μg) was digested to completion with AccI, and the ends were filled in with *E. coli* DNA polymerase I large fragment (Klenow polymerase). The synthetic ANF gene was excised by digestion of pANF-1 with DdeI and Hinc II. After filling out the Dde1 end with Klenow polymerase, the 104 bp fragment was isolated. The ANF gene fragment was then ligated to pSC1N treated as described above and used to transform competent JM105 cells. Ampicillin-resistant colonies were screened with an appropriate oligonucleotide. SDS extracts of hybridization positive colonies were electrophoresed on a 15% sodium dodecyl sulfate polyacrylamide gel (SDS-PAGE), followed by either staining with Coomassie Blue or protein blot analysis to detect the expression of the fusion protein.

Figure 6:
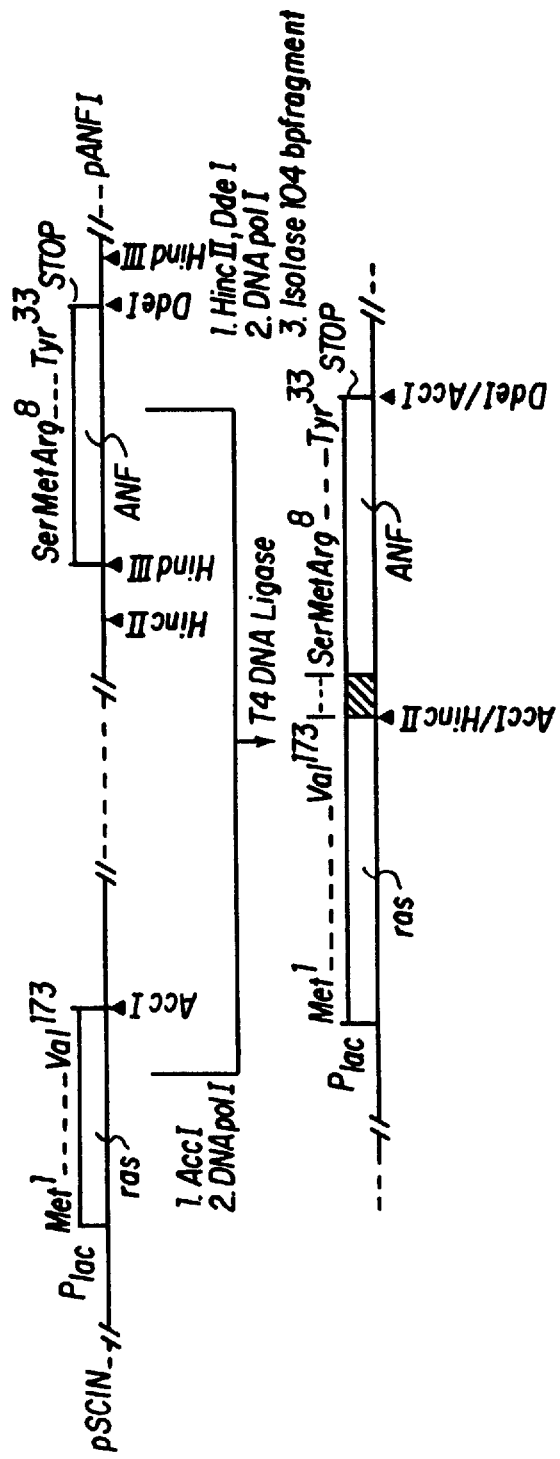
FIG. 6 is a diagram of the pSC1N plasmid.

The ANF gene was transferred from the pSCN1 plasmid to the pLC1-28 plasmid. Plasmid pLC1-28 is a col E1-derived plasmid that contains the entire Che operon and is described in Matsumura, et al., J. Bacteriol. 160:36–41 (1985). The Che operon fragment containing the CheY and CHEZ genes was excised from pLC1-28 as a BamHI-HindIII fragment and sub-cloned into BamHI-Hind III digested pUC13(PL Biochemicals) to give pUC13-CheY-CheZ. *E. coli* JM105 clones transfonned by pUC13-CheY-CheZ expressed CheY and CheZ polypeptides off the lac promoter contributed by the pUC13 vector. To construct an expression plasmid for the CheY-(rat-ANF-26) fusion, pUC13-CheY-CheZ was digested at the unique PstI site internal to the CheY coding region and at the unique Sma1 site in the pUC13 polylinker 3' to the inserted Che DNA. The resulting 3 kb PstI-SmaI fragment containing the pUC13 vector and the DNA encoding the N-terminal 100 residues of CheY was recombined with the 160 bp Pst I-HindIII fragment of pSCN1-(rat-ANF-26) that encodes the Met-(rat-ANF-26) sequence and contains 50 bp of untranslated RAS1 sequence 3' to the termination codon for the ANF peptide, see FIG. 6. *E. coli* JM 105 was transformed with the ligation mix containing the two fragments described above. DNA was isolated (minipreps) from ampicillin-resistant clones. The desired clones were identified as those releasing a 160 bp gene fragment upon EcoRI-Pst I digestion. These clones were shown to express ANF peptides by Western Blot analysis of total cellular protein using anti-ANF antisera.

EXAMPLE 11

Construction of Plasmid pJC264

The CheY-ANF plasmid from Example 10 was converted to the plasmid pJC220 which was in turn modified to produce the unique pJC264 plasmid. To convert CheY-ANF to PJC220, 40 μg of CheY-ANF plasmid DNA was incubated at 37° C. with 20 units of HindIII (International Biotechnologies, Incorporated) in a final volume of 200 μl of 25 mM Tris-HCl pH 7.8, 50 mM NaCl, 10 mM $MgCl_2$, 1 mM DTT, and 100 μg/ml bovine serum albumin. At 15 minute intervals 50 ml aliquots were transferred to tubes containing 2 μl 0.5M Na-EDTA, pH 8.0 to stop the digestion. Each sample 150 ng was electrophoresed in adjacent lanes of a 0.7% (w/v) Seaplaque agarose (FMC) gel containing 89 mM TRIS, 89 mM boric acid, 2 mM EDTA (TBE) and 0.5 mg/ml ethidium bromide. The linearized plasmid was identified as that band comigrating with XhoI-digested CheY-ANF when visualized by 365 nm light. This band was excised from the gel with a razor blade from the lanes corresponding to 15, 30, 45 and 60 minutes of digestion, melted at 65° C., and diluted with 10 volumes of 0.2M NaCl, 10 mM Tris-HCl pH 7.2, 1 mM EDTA, at 37° C. (Buffer A). The DNA was bound to a NACS Prepac cartridge (Bethesda Research Laboratories) BRL by gravity flow, washed with 10 ml Buffer A, and eluted with 0.5 ml Buffer D (2M NaCl, 10 mM Tris-HCl pH 7.2, 1 mM EDTA) by gravity flow. One ml absolute ethanol was added to the column eluate. The sample was mixed and incubated on dry ice 10 minutes and centrifuged at 12,000×g for 15 minutes at 4° C. The supernatant fluid was decanted, the precipitate was washed with 0.5 ml 70% ethanol and dried in vacuo. After dissolving the pellet in TE (10 mM Tris-HCl pH 7.4, 1 mM EDTA), the DNA content was measured by the ethidium bromide spot test, agarose plate method (Maniatis, et al., Molecular Cloning: A Laboratory Manual, Cold Spring Harbor Laboratory (1982) p. 468–469).

The ends of the linearized plasmid DNA were made blunt by incubating 30 ng for 2 hours at 15° C. in a 25 μl reaction mix containing 20 mM each of dATP, dGTP, dCTP, and TTP, 60 mM NaCl, 6 mM Tris-HCl pH 7.5, 6 mM $MgCl_2$, 1 mM DTT, and 22.5 units of DNA Polymerase I, large (Klenow) fragment (Boehringer-Mannheim). The reaction was terminated and the DNA purified by extraction with phenol/chloroform (Maniatis, et al., supra, p. 458–459) and ethanol precipitation (Maniatis, et al., supra, p. 461).

BamHI linkers (d-GGGATCCC, Boehringer-Mannheim), 12.5 μg, were phosphorylated with 40 units of T4 polynucleotide kinase (Pharmacia) in a 40 ml reaction mixture containing 50 mM Tris-HCl pH 7.4, 10 mM $MgCl_2$, 5 mM DTT, 500 μM ATP, and 40 μCi of q-$^{32}$ P-ATP (Amersham, 5000 Ci/mmol, 10 mCi/ml), for 30 minutes at 37° C. The reaction was stopped by incubating at 70° C. for 5 minutes, and the linkers were stored at −20° C. until used.

The blunt-ended, linearized plasmid DNA was dissolved in 6.6 ml water and adjusted to a 10 ml final volume containing 125 ng phosphorylated BamHI linkers, 6.6 mM Tris-HCl pH 7.5, 6.6 mM $MgCl_2$, 1 mM ATP, 10 mM DTT, and 0.0025 units T4 DNA ligase (New England Biolabs). After incubating 18 hours at 4° C., 5 μl of this mixture were added to 100 μl competent *E. coli* HB101 cells (BRL). Transformation of cells was performed according to the method provided by BRL. Eleven ampicillin-resistant colonies were chosen at random and each was used to inoculate 5 ml liquid culture of LB broth (Maniatis, et al., supra) containing 100 μg/ml ampicillin. After overnight growth at 37° C., plasmid minipreps were made as described by Ish-Horowicz and Burke, Nucleic Acids Research 9:2989–2998 (1981).

By restriction enzyme mapping and agarose gel analysis, one plasmid, designated pJC220, was found to have a BamHI linker in place of the promoter-proximal HindIII site. This plasmid was also shown to retain the HindIII site (now unique) at the 3' end of the CheY coding region.

The pJC220 plasmid was converted to the pJC264 plasmid by digestion of 10 mg of pJC220 DNA with 50 units of HindIII (Boehringer-Mannheim) for 1 hour at 37° C. in a 50 ml solution containing 50 mM NaCl, 10 mM Tris-HCl pH 7.4, 10 mM MgSO$_4$, and 1 mM DTT. Ammonium acetate was added to 2.5M final concentration, and the DNA recovered by precipitation with 2 volumes of ethanol. The HindIII digested DNA was then partially filled in with 5 units of the large fragment of DNA polymerase I (Boehringer-Mannheim) in a 20 ml solution containing 20 μM each dATP and dGTP, 60 mM NaCl, 6 mM Tris-HCl, pH 7.5, 6 mM MgCl$_2$, and 1 mM DTT, and incubated 30 minutes at room temperature. The sample was extracted with phenol/chloroform and recovered by ethanol precipitation as described by Maniatis et al.

The DNA was dissolved in water and adjusted to 0.3M NaCl, 30 mM Na acetate pH 4.6, and 4.5 mM ZnCl$_2$, in a final volume of 20 ml. Five units of S1 nuclease (BRL) were added and the mixture incubated at 37° C. for 30 minutes. Digestion was stopped by adding 1 μl 0.5M EDTA pH 8.0, and the DNA was phenol/chloroform extracted and ethanol precipitated. The S1-nuclease treated DNA was digested with 80 units of EcoRI (New England Biolabs) in 50 μl of buffer containing 100 mM NaCl, 50 mM Tris-HCl pH 7.4, and 10 mM MgSO$_4$, for 30 minutes at 37° C. DNA was recovered by ethanol precipitation in ammonium acetate as described above. The EcoRI ends were filled in with the large fragment of DNA polymerase I as described above, but in the presence of dATP and TFP and in the absence of dGTP and dCTP. DNA was extracted with phenol/chloroform and recovered by ethanol precipitation.

One hundred ng of this DNA were ligated for 24 hours at 4° C. in 10 μl of solution containing 66 mM Tris-HCl pH 7.5, 6.6 mM MgCl2, 10 mM DTT, 1 μM ATP, and 400 units T4 DNA ligase (New England Biolabs). Two μl of ligation mix were used to transform 100 μl of competent E. coli JM109 cells (Stratagene) using the supplier's standard procedure. Ampicillin-resistant transformants were screened by colony hybridization using a 5'-$^{32}$P-labeled synthetic oligonucleotide d(CCCAAGAATTCACTGG) as a probe, using standard methods of Mason & Williams, in "Nucleic Acid Hybridization: A Practical Approach, B. D. Hames and S. J. Higgens, eds. IRL Press (1985), p. 113–137. One hybridizing colony, designated pJC264, was shown by restriction mapping to have reconstructed a unique EcoRI site at the 3' end of the CheY gene.

The construction of pJC264 from CheY-ANF can be seen schematically in FIG. 7 and the restriction map of pJC264 is shown in FIG. 8.

EXAMPLE 12

Subcloning cDNA Inserts Into pJC264

Twenty micrograms of pJC264 from Example 11 was linearized with EcoRI using the reaction conditions described in Example 8. The reaction product was precipitated, washed twice with 70% EtOH and suspended in 43 μl of distilled water and 5 ml of 10× CIP buffer (0.5 M Tris-HCl, pH 9.0, 10 mM MgCl$_2$, 1 mM ZnCl$_2$, 10 mM spermidine). The 5'-phosphate from the EcoRI ends were removed with calf intestinal alkaline phosphatase (Boehringer-Mannheim). One microliter of enzyme (19 U/ul) was added to initiate the reaction at 37° C. for 30 minutes and then a second microliter was added for an equivalent length of time. The reaction was stopped by the addition of 42.5 ml distilled water, 2.5 ml 20% sodium dodecyl sulfate (SDS), 10 ml 10× STE (100 mM Tris-HCl, pH 8.0/1M NaCl/10 mM EDTA) and heated at 68° C. for 15 minutes. The reaction mixture was extracted 2× with phenol/chloroform/isoamyl alcohol (48:48:2), twice with chloroform/isoamyl alcohol (24:1), and the final aqueous phase was passed through a 1 cc column bed of Sephadex G-25 (medium) equilibrated in TE by centrifugation at 1000×g for 5 minutes at room temperature (spin-column). The DNA was then precipitated as described earlier, washed twice with 70% EtOH, suspended in 50 μl of TE and quantitated by absorbance at 260 nm.

Approximately 100 ng of EcoRI linearized and phosphatased pJC264 was mixed with an equimolar amount of gel purified E. tenella cDNA insert in a 20 ml reaction mixture which, in addition, consisted of 66 mM Tris-HCl, pH 7.6, 5 mM MgCl$_2$, 5 mM DTT, 1 mM ATP. The reaction was initiated by the addition of 1 μl of T4 DNA ligase (New England Biolabs, 200–400 U/ul) and proceeded at 14° C. for 12–16 hours.

A predetermined volume (3 ml per transformation reaction) of 2×YT bacterial media (16 g bactotryptone/10 g yeast extract/5 g NaCl per liter) was inoculated with a single colony of E. coli JM83 and grown with vigorous mixing at 37° C. until it reached an optical density at 600 nm of 0.6. Bacteria were collected by centrifugation at 1000×g at 4° C. for 5 minutes and gently suspended in one-half of the original culture volume with sterile 50 mM CaCl$_2$. The suspension was kept on ice for 20 minutes and the bacterial cells were collected by centrifugation as above. The pellet was then gently suspended in one-tenth volume of sterile 50 mM CaCl$_2$. The bacterial suspension was then kept at 4° C. for 16–24 hours.

The 20 μl ligation reaction mixture was diluted to 100 μl by the addition of 80 μl of sterile TE, and 5 ml and 95 ml aliquots were dispensed to sterile polypropylene tubes. Approximately 200 μl of competent bacteria were added to each of the tubes containing the ligation reactions (as well as the appropriate ligation and transformation controls) and these were placed on ice for 40 minutes. After this, the bacteria were "beat-shocked" by incubation at 42° C. for 90 seconds. Each transformation tube was then plated onto a 2×YT agar plate which contained ampicillin at a concentration of 50 μg/l for the selection of bacteria harboring plasmids and for plasmid maintenance. Plates were incubated in an inverted position overnight at 37° C.

Bacterial clones harboring plasmids were identified by their ability to grow on plates in the presence of drug selection. Single colonies were used to inoculate 50 ml of 2×YT/AMP (i.e., 2×YT media containing ampicillin at 50 μg/L) and these cultures were grown overnight at 37° C. with vigorous shaking. Approximately 1.5 μl of the culture was poured off into an Eppendorf tube and collected by centrifugation in an Eppendorf centrifuge for at least 1 minute; the remainder of the culture was stored at 4° C. and served as a genetic stock. The media above the bacterial pellet was aspirated off and the pellet was suspended by vortexing in 100 ml of a cold, freshly prepared solution of 50 mM glucose, 10 mM EDTA, 25 mM Tris-HCl (pH 9.0), 4 mg ml-1 lysozyme. This mixture was incubated at room temperature for 5 minutes. Then 200 ml of a cold, freshly prepared solution composed of 0.2N NaOH and 1% SDS was added to each tube, mixed gently by inversion, and put on ice for 5 minutes. To this mixture was added 150 μl of a cold, freshly prepared solution containing 6 ml of 5M potassium acetate, 1.15 ml of glacial acetic acid, 2.85 ml distilled water. The contents were gently mixed on a vortex mixture and this mixture was stored on ice for 5 minutes.

The cellular debris was collected by centrifugation in an Eppendorf centrifuge for 10 minutes at 4° C. and the supernatant was extracted one time with phenol/chloroform/isoamyl alcohol (25:24:1). Plasmid DNA and cellular RNA were precipitated from the final aqueous phase with the addition of two volumes of room temperature 100% ethanol. A pellet was collected by centrifugation for 5 minutes at room temperature, the pellet was washed one time with 70% ethanol and then dried briefly. The nucleic acid pellet was then suspended in 50 ml of TE containing 20 µg of DNase-free RNase per µl and incubated for 15–30 minutes at 37° C. to quantitatively eliminate cellular RNA. Aliquots of 10 µl were then cut to completion with EcoRI (approximately 20 units) in a buffer composed of 50 mM NaCl, 100 mM Tris-HCl (pH 7.5), 5 mM $MgCl_2$ at 37° C. for 60 minutes. The restriction enzyme reaction products were fractionated by agarose gel electrophoresis to identify those plasmids which contained the appropriate inserts. Those recombinant plasmids which contained the predicted EcoRI insert were then cut with a second restriction enzyme (usually Pst I) to verify (i) that only a single copy of the insert was contained within the plasmid, and (ii) to score for orientation of the insert DNA with respect to the bacterial promoter. This was accomplished by removing a second 10 µl aliquot from the remaining 40 µl of RNase-digested bacterial nucleic acid and cutting it in a buffer composed of 100 mM NaCl, 10 mM Tris-HCl (pH 7.5), and 10 mM $MgCl_2$ with approximately 20 units of PstI for 60 minutes at 37° C. Again, the restriction enzyme digests were resolved by agarose gel electrophoresis.

EXAMPLE 13

Production of Eimeria-CheY Fusion Proteins

An overnight culture of selected recombinant bacteria was prepared by inoculating 5 ml of broth with a single colony of bacteria. The culture medium was 2×YT (16 g tryptone, 10 g yeast extract, 10 g NaCl/liter) containing ampicillin (50 µg/ml). The overnight culture was used to inoculate 500 ml of 2×YT containing ampicillin. The culture was grown at 37° C. with aeration until mid-log growth was reached (A550Z0.5) at which point IPTG was added to a final concentration of 100 mM. The culture was grown for a further 3–4 hours at 37°, chilled on ice, and centrifuged for 15 minutes at 4° C. The cells were washed once with PBS, then the bacteria were collected by centrifugation and were stored frozen at −70° C. until needed. When needed, the bacterial pellets were thawed and suspended in 10 ml of 30 mM Tris-HCl, pH 8.0, 50 mM EDTA and 1 mM phenylmethyl-sulphonylfluoride (Buffer A). The suspension was sonicated on ice twice, each time for three minutes, using a Branson cell disrupter Model 350 (duty cycle 30, output control 4). The sonicate was clarified by centrifugation at 27000×g for 45 minutes at 4° C. The supernatant fluid constituted the first supernatant. The pellet of insoluble material was washed in 10 ml of buffer A containing 0.1% w/v Triton X100. The suspension was stirred in an ice-bath for 30 minutes prior to centrifugation at 27,000×g for 45 minutes and at 4° C. The supernatant fluid is designated the second supernatant. The pellet (P2) was then washed twice in Buffer A and the wash discarded. Pellet (P2) was suspended in 1.0 ml of 6M guanidine-HCl containing 100 mM DTT and the suspension was incubated for 2 hours at 50° C. The suspension was diluted to 10 mls with 7M urea and was clarified by centrifugation at 27000×g for 45 minutes at 4° C. The supernatant fluid constituted the third supernatant. Different fusion proteins exhibited different solubility properties, some were found predominantly in the first supernatant, some in the second, and some (most commonly) were found in the third.

The SO6-CheY antigen (recombinant A antigen) was found in the first, second, and third supernatant. Material for in vivo testing was prepared from the third supernatant by ion exchange chromatography. A Trisacryl M-DEAE (LKB) column (5 mls) equilibrated in 0.025M Tris-HCl, pH 8.5, 8M urea was prepared. From the third supernatant, a 2 ml sample, containing 12 mg protein, was dialyzed against 100 ml of the above buffer, and was then applied to the column. The column was washed with one column volume of column buffer, prior to step-wise elution with column buffer containing 0.05M, 0.1M, 0.15M, 0.2M, 0.25M, 0.3M, 0.35M, or 0.4M NaCl. Each elution was performed with two column volumes. Eluates were tested for the presence of recombinant protein by SDS-PAGE and Western blotting, using rabbit anti-Fraction V. The SO6/CheY protein was found to elute in the 0.15M and 0.20M NaCl fractions. Fractions were pooled, dialyzed against 50 mM NH4CO3, and were freeze dried. The yield of protein from a 500 ml culture is approximately 3 mg.

The SO7-CheY fusion protein (recombinant B antigen) was found in the third supernatant. Further purification was obtained by chromatography on hydroxyapatite. A column of hydroxyapatite (6 ml bed volume; BioRad Labs; HPT grade) was equilibrated in 7M urea, and the third supernatant was applied to the column. After washing the column with one bed volume of 7M urea, the flow-through and wash were combined, concentrated to 10 ml on Amicon diafiltration membrane YM10, dialyzed against 50 mM NH4HCO3, and were freeze dried (including any precipitate that formed). The yield from a 500 ml culture was approximately 35 mg protein.

The SP54-CheY fusion protein (recombinant C antigen) was also found in the third supernatant. Further purification was unnecessary for in vivo testing. The yield of protein in the third supernatant from a 500 ml culture was approximately 170 mg.

The SO311-CheY fusion protein (recombinant H antigen) was also found in the third supernatant. Further purification was obtained by chromatography on hydroxyapatite. The column was prepared as described above, and the third supernatant applied. The column was developed with two bed volumes of 7M urea, then 2 bed volumes of 7M urea containing 10 mM, 20 mM, 40 mM, 80 mM, 160 mM or 320 mM sodium phosphate buffer, pH 6.5. Column eluates were tested for the presence of recombinant protein by SDS-PAGE and Western blotting, using rabbit anti-fraction V, rabbit anti-sporozoite serum, or recombinant eluted antibodies. The SO311/CheY protein was found in the 40 mM, 80 mM and 160 mM eluates. These eluates were pooled, concentrated, dialyzed and freeze-dried exactly as above. The yield from a 500 ml culture was approximately 5 mg protein.

The SO216-CheY fusion protein (recombinant F antigen) was also found in the third supernatant fluid. No further purification was necessary for in vivo testing. The yield from a 500 ml culture was approximately 30 mg protein.

EXAMPLE 14

Characterization of Recombinant-Derived *E. tenella* Immunogens

Representative *E. tenella* immunogen clones, from Example 9, were subjected to nucleotide sequence analysis utilizing one or two of three standard methodologies. Some sequence analyses were determined using the chemical degradation method of Maxam and Gilbert, Methods in Enzymology, 65 (part 1): 497–559 (1980). More commonly, the nucleotide sequence was determined by the dideoxy chain termination technique, using denatured plasmid templates (plasmid pUC18, containing assorted subsequences of the E. tenella cDNAs) as described by Hattori and Sakaki, Analyl. Biochem. 152: 232–238 (1986). The third approach to nucleotide sequence determination was accomplished by subcloning the cDNA insert, or portions of it, into bacteriophage mp18 and sequencing secreted single-stranded recombinant phage templates using the standard dideoxy chain-termination sequencing methodology of Messing, Methods in Enzymology 101: 20–78 (1983). In addition to AMV reverse transcriptase and the Klenow fragment of DNA polymerase I, a modified T7 DNA polymerase has been employed, see Tabor and Richardson, Proc. Nat. Acad. Sci. U.S.A. 84: 4767–4771 (1987).

The amino acid sequences were deduced from the determined nucleotide sequences by combining the following information. Each of the cDNAs, see Example 8, in the phage expression vector λgt11 was identified by polyclonal antisera, see Example 2, when expressed as a fusion protein with β-galactosidase. The nature of the covalent attachment of this fusion protein is shown in the following table.

TABLE 5

| Beta-galactosidase | EcoRI Cloning Site EcoRI | E. tenella |
|---|---|---|
| 5' | GCG GAA TTC<br>Ala Glu Phe | 3' |

This junction (and reading frame, cloning site) at the EcoRI cleavage site, is regenerated in each subsequent cloning event involving the entire cDNA irrespective of the subcloning vector, pUC18, mp18 or pJC264. Consequently, the reading frame can be unequivocally identified and the nucleotide sequence translated once the orientation of the insert in these three vectors is established. The orientation of the cDNA insert in plasmid, puc 18 and pJC264, or phage, mp18, vectors is accomplished by restriction enzyme mapping, see Example 9. Once asymmetric restriction enzyme recognition sequences are identified within the cDNA insert, insert orientation and transcriptional orientation can be unequivocally assigned when the recognition sequences are similarly predicted by the nucleotide sequence.

Group A clone nucleotide sequences and the resulting Group A immunogen amino acid sequences are exemplified by the representative clone SO67. This clone is entirely contained within the SO6 clone. Of the approximately 870 nucleotides in this clone the first 162 nucleotides starting at the 5' end have been sequenced. The transcriptional orientation and therefore the correct reading frame can be deduced unambigiously based upon the location in the nucleotide sequence of restriction enzyme recognition sequences which are predicted by restriction enzyme mapping of the CheY-SO67 recombinant plasmid. The nucleotide sequence and the resulting 53 N-terminal amino acid sequence is shown in the following table.

TABLE 6

N-Terminal Nucleotide And Deduced Amino Acid Sequence of Group A Immunogen SO67

```
              10              20              30              40              50
              *               *               *               *               *
T  TTA TTC CTT CGA TGC CTG GCG GCG TTG TTC ATC ATG TTC ATC ACG AGG CGC CTT CTG
   Leu Phe Leu Arg Cys Leu Ala Ala Leu Phe Ile Met Phe Ile Thr Arg Arg Leu Leu
                                       10

60              70              80              90             100             110
       *               *               *               *               *               *
   CTG CTG CGA TTC ACC GTT CCT ACC GTG CTT TGC TGC TGC AGC AGC AGC ANG TGC TCG
   Leu Leu Arg Phe Thr Val Pro Thr Val Leu Cys Cys Cys Ser Ser Ser XXX Cys Ser
   20                                              30

120             130             140             150             160
           *               *               *               *               *
   TCG ANG NAG AGC GCC GGG GCA GCA GAA GCA GCA GCA GCA GCA GCT CG
   Ser XXX XXX Ser Ala Gly Ala Ala Glu Ala Ala Ala Ala Ala Ala
       40                                          50
```

An additional 221 nucleotide sequence has been obtained from the 3' end of the clone, see table 7 below, but the reading frame has not been deduced.

TABLE 7

3' Nucleotide Sequence of Group A Immunogen SO67

| | |
|---|---|
| 1 | CGAGTGGCTG GTTGACACCG GCAGGGTCTT CGCCGGCGGC GTTGCTAGCA TAGCCGACGG |
| 61 | CTGCCGGCTC TTCGGAGCAG CAGTGGAGGG CGAGGGCAAC GCTGGGAAGA ACTCGTCAAG |
| 121 | ACCAACTACC AAATTGAAGT CCCCCAGGAA GACGGAACCT CCATTTCAGT GGATTGCGAC |
| 181 | GAGGCGGAGA CTCTGCGGCA GGCGGTGGTG GACGGCCGCG C |

Group B clone nucleotide sequence and the resulting Group B immunogen amino acid sequence are exemplified by the representative clone SO7. The reading frame can be deduced unambiguously by correlating the position of restriction enzymes sites asymmetrically located within the cDNA with the location of their respective recognition sequences as predicted by the nucleotide sequence analysis. All 957 nucleotides in this clone have been sequenced. The nucleotide sequence and the amino acid sequence up to the termination codon at base 713 are shown in the following table.

TABLE 8

Nucleotide And Deduced Amino Acid Sequence of Group B Immunogen SO7

```
                    10              20              30              40              50
                    *               *               *               *               *
T  CTC GCC CCA ACT TTT TCC CCC GCG CTC CGC  AGC AGC AGC AGC AGC AGC AGC AGC AGC
   Leu Ala Pro Thr Phe Ser Pro Ala Leu Arg  Ser Ser Ser Ser Ser Ser Ser Ser Ser
                                        10

60              70              80              90             100             110
       *               *               *               *               *               *
   AGC AAA ATG GCA GAC CTC TTC AGC GGA CTC  GTG GGC GGC GTC GTC GGC GCT GTT GCT
   Ser Lys Met Ala Asp Leu Phe Ser Gly Leu  Val Gly Gly Val Val Gly Ala Val Ala
   20                                            30

120             130             140             150             160             170
   *               *               *               *               *               *
   GCA GCA GAT TTG CCT GCG GAG GGC GAG AGG  GCC CCC CGC CCC GCC CCC GGC ACT GCC
   Ala Ala Asp Leu Pro Ala Glu Gly Glu Arg  Ala Pro Arg Pro Ala Pro Gly Thr Ala
           40                                        50

180             190             200             210             220
               *               *               *               *               *
   TGG ACT TGC TGC TGC AGC AAA CTG CAA GAA  GGG GCC CGC GAG CTG GAG GGT TTT GTG
   Trp Thr Cys Cys Cys Ser Lys Leu Gln Glu  Gly Ala Arg Glu Leu Glu Gly Phe Val
           60                                        70

230             240             250             260             270             280
   *               *               *               *               *               *
   CAG CAG CTG AGT TTT GTT GCA GGG AAG CTG  GCC TGC TGC CTG CGG GTG GGG GCG GAG
   Gln Gln Leu Ser Phe Val Ala Gly Lys Leu  Ala Cys Cys Leu Arg Val Gly Ala Glu
               80                                        90

290             300             310             320             330             340
           *               *               *               *               *               *
   CAG CTG GCG CGC TGC GCT GCG GAG GGG CGG  CTG CCC AGC AGC AGC AGC AGC AGC AGC
   Gln Leu Ala Arg Cys Ala Ala Glu Gly Arg  Leu Pro Ser Ser Ser Ser Ser Ser Ser
                       100                                      110

350             360             370             380             390             400
                   *               *               *               *               *               *
   TGC TGC GCG CTG CTG CAG CTC GAG AAG CAG  GAC CTC GAG CAG AGC CTC GAG GCC GGC
   Cys Cys Ala Leu Leu Gln Leu Glu Lys Gln  Asp Leu Glu Gln Ser Leu Glu Ala Gly
                           120                                      130

410             420             430             440             450
                       *               *               *               *               *
   AAG CAG GGC GCG GAG TGC CTC TTG AGG AGC  AGC AAA CTG GCC CTC GAG GCC CTC CTC
   Lys Gln Gly Ala Glu Cys Leu Leu Arg Ser  Ser Lys Leu Ala Leu Glu Ala Leu Leu
                               140                                      150

460             470             480             490             500             510
           *               *               *               *               *               *
   GAG GGG GCC CGC GTT GCA GCA ACG CGG GGT  TTG CTG CTG GTC GAG AGC AGC AAA GAC
   Glu Gly Ala Arg Val Ala Ala Thr Arg Gly  Leu Leu Leu Val Glu Ser Ser Lys Asp
                           160                                      170
```

TABLE 8-continued

Nucleotide And Deduced Amino Acid Sequence of Group B Immunogen SO7

```
          520                 530                 540                 550                 560                 570
           *                   *                   *                   *                   *                   *
ACG GTG CTG CGC AGC ATT CCC CAC ACC CAG GAG AAG CTG GCC CAG GCC TAC AGT TCT
Thr Val Leu Arg Ser Ile Pro His Thr Gln Glu Lys Leu Ala Gln Ala Tyr Ser Ser
                                        180                                                                 190

580                 590                 600                 610                 620
                   *                   *                   *                   *                   *
TTC CTG CGG GGC TAC CAG GGG GCA GCA GCG GGG AGG TCT CTG GGC TAC GGG GCC CCT
Phe Leu Arg Gly Tyr Gln Gly Ala Ala Ala Gly Arg Ser Leu Gly Tyr Gly Ala Pro
                                                200

630                 640                 650                 660                 670                 680
  *                   *                   *                   *                   *                   *
GCT GCT GCT TAC GGC CAG CAG CAG CAG CCC AGC AGC TAC GGG GCG CCC CCC GCC TCC
Ala Ala Ala Tyr Gly Gln Gln Gln Gln Pro Ser Ser Tyr Gly Ala Pro Pro Ala Ser
210                                                      220

690                 700                 710                 720                 730                 740
           *                   *                   *                   *                   *                   *
AGC CAG CAG CCC TCC GGC TTC TTC TGG TAG CCC TGC AGC AGC AGC AGC AGC AGC AGC
Ser Gln Gln Pro Ser Gly Phe Phe Trp ---
    230

750                 760                 770                 780                 790
                   *                   *                   *                   *                   *
AGC AGC AGC AGC GCG GGC GGC AGC CGC GGC GGG GCC GGG GCG CCG CTG CAG CAA CAG 800                 810                 820                 830                 840                 850
 *                   *                   *                   *                   *                   *
CAG CAG CCG n n n CGG CTA GCG CCG CGG AGC ACT CGC AGG GAA CTC CAC AGG CAG CGG 860                 870                 880                 890                 900                 910
           *                   *                   *                   *                   *                   *
GAG AGC AGC AGG GAC GAG AAG CAG GTC ATG TAG CGC AGG CAG CAG CGC CAG CTG CAG 920                 930                 940                 950
                   *                   *                   *                   *
CAG CAG CAG CAG CAG CAG CAG CAG CAG CAG CAG CTC CTG CAC CG
```

Group C clone nucleotide sequence and the resulting Group C immunogen amino acid sequence are exemplified by the representative clone SP54, see Example 9. This clone is entirely contained within the SP59 clone, see Example 9. Of the approximately 700 nucleotides in this clone the first 157 nucleotides starting at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping of the CheY-SP54 recombinant plasmid. The nucleotide sequence and the resulting 52 amino acid sequence is shown in the following table.

TABLE 9

N-Terminal Nucleotide and Deduced Amino Acid Sequence of Group C Immunogen SP54

```
                    10                  20                  30                  40                  50
                     *                   *                   *                   *                   *
C  GCG GAA TCC GCA GAC ACT GCT GAG ATC CGC GTG CCC GTG GGG GCC ACT GTG GTG GTG
   Ala Glu Ser Ala Asp Thr Ala Glu Ile Arg Val Pro Val Gly Ala Thr Val Val Val
                                            10

60                  70                  80                  90                  100                 110
             *                   *                   *                   *                   *                   *
   CGG CTT CAG AGC GTT GGG GGC TAC AGG CCA GTG TTG GTG AGT GCC CAG AGT GGG GCT
   Arg Leu Gln Ser Val Gly Gly Tyr Arg Pro Val Leu Val Ser Ala Gln Ser Gly Ala
   20                                              30

120                 130                 140                 150
                     *                   *                   *                   *
   GTG GGC CTC TCC GAG CTT TCC CAG GCT TCC CCC AGT TCG GCC
   Val Gly Leu Ser Glu Leu Ser Gln Ala Ser Pro Ser Ser Ala
       40                                              50
```

Group H clone nucleotide sequence and the resulting Group H immunogen amino acid sequence is exemplified by the representative clone SO311, see Example 9. Of the approximately 650 nucleotides in this clone, the first 185 nucleotides starting at the 5' end have been sequenced. The transcriptional orientation and therefore the appropriate reading frame can be unequivocally deduced by correlating restriction enzyme recognition sequences in the nucleotide sequence with their asymmetric location predicted by restriction enzyme mapping. The nucleotide sequence and the resulting 61 amino acid sequence is shown in the following table.

TABLE 10

N-Terminal Nucleotide and Deduced Amino Acid Sequence of Group H-Immunogen SO311

|   |     |     |     |     |     |     |     |     |     |     |     |     |     |     |     |     |     |     |
|---|-----|-----|-----|-----|-----|-----|-----|-----|-----|-----|-----|-----|-----|-----|-----|-----|-----|-----|
|   |     |     | 10  |     |     |     | 20  |     |     |     | 30  |     |     |     | 40  |     |     | 50  |
|   |     |     | *   |     |     |     | *   |     |     |     | *   |     |     |     | *   |     |     | *   |
| C | CTG | GCC | ACA | GGG | CTC | CTG | TTC | GCC | AAC | AGC | CTG | CTG | CGA | CAT | GGA | TCT | GTC | AGA | GTG |
|   | Leu | Ala | Thr | Gly | Leu | Leu | Phe | Ala | Asn | Ser | Leu | Leu | Arg | His | Gly | Ser | Val | Arg | Val |
|   |     |     |     |     |     |     |     |     |     | 10  |     |     |     |     |     |     |     |     |     |

|     |     |     |     |     |     |     |     |     |     |     |     |     |     |     |     |     |     |
|-----|-----|-----|-----|-----|-----|-----|-----|-----|-----|-----|-----|-----|-----|-----|-----|-----|-----|
| 60  |     |     |     | 70  |     |     |     | 80  |     |     |     | 90  |     |     |     | 100 |     | 110 |
| *   |     |     |     | *   |     |     |     | *   |     |     |     | *   |     |     |     | *   |     | *   |
| GCA | CAT | TGT | GAA | TGC | AAT | TCT | GTG | CGG | GTC | TCT | TGC | GGC | CGC | TGC | TCA | CTT | CGC | CAC |
| Ala | His | Cys | Gly | Cys | Asn | Ser | Val | Arg | Val | Ser | Cys | Gly | Arg | Cys | Ser | Leu | Arg | His |
| 20  |     |     |     |     |     |     |     |     |     | 30  |     |     |     |     |     |     |     |     |

|     | 120 |     |     | 130 |     |     | 140 |     |     | 150 |     |     | 160 |     |     | 170 |     |
|-----|-----|-----|-----|-----|-----|-----|-----|-----|-----|-----|-----|-----|-----|-----|-----|-----|-----|
|     | *   |     |     | *   |     |     | *   |     |     | *   |     |     | *   |     |     | *   |     |
| GAA | AGT | CAA | CCC | CAG | GGC | TAT | GCA | AGC | TGG | ATT | CAG | AGT | ATA | CAA | GGC | CGA | AAC | TTC |
| Glu | Ser | Gln | Pro | Gln | Gly | Tyr | Ala | Ser | Trp | Ile | Gln | Ser | Ile | Gln | Gly | Arg | Asn | Phe |
|     | 40  |     |     |     |     |     |     |     |     |     | 50  |     |     |     |     |     |     |     |

|     | 180 |     |     |
|-----|-----|-----|-----|
|     | *   |     |     |
| AAT | GCG | CGA | GCT | C |
| Asn | Ala | Arg | Ala |
|     |     | 60  |     |

An additional 283 nucleotide sequence has been obtained from the 3' end of the clone, see table below, but the reading frame has not been deduced. Linker nucleotides are included in positions 1–8.

TABLE 11

3' Terminal Nucleotide Sequence of Group H Immunogen SO311

| | |
|---|---|
| 1 | GAATTCGGGT TATCCACATC ACGGTGGACG TCTGATTTAG CGGAGGAGGT ATGAACCCTC |
| 61 | AGAGCCAGCC CAGTAGGAAG CATTCATCCA TCTTGGTCTT TGCTCCCACA GACGGTGCAG |
| 121 | GATTTCGAGG AGAGAGTGTA TCATTCCTCT CAGTGTTGGG ATGACATTCT CAGATGCGCG |
| 181 | CATCACGTAA TGATAGCCAT TCCTGCTCCA GTCGGAAGCT ATGTCCTGAC TCTGGAGAGC |
| 241 | AGCATTTCGG CGTGATACTT GAGCTTGTCA GAGATAGCCA GCTGCTTCGA G |

Group F clone nucleotide sequence of the Group F immunogen is exemplified by the representative clone SO216, see Example 9. The approximately 487 nucleotides, including eight linker nts at each end, have been sequenced. The sequence is given in the following table.

TABLE 12

Nucleotide Sequence of Group F Immunogen SO216

| | |
|---|---|
| 1 | GAATTCGGGC AGAAAACAAT TACTGAAAGA CGGAGGGAAA GTGTCTCGCC GGCAAAGTTA |
| 61 | AGCGAACGGA CTGATTTGGA AATAGGGTCT TGCTGCGCAA ACGAATGCTG CAAATGCATC |

TABLE 12-continued

Nucleotide Sequence of Group F Immunogen SO216

| | |
|---|---|
| 121 | CCAAAGCGGT ACCGCGATGG ATCAGCAAGA AAAACNCCTC AGTGAAACGA TAGGAGCTGA |
| 181 | TGCCGAAGTC CGCACAGCAT GATCTATGTC TCATCGCTGC TGAGTTAGCT ACTGAGGCCA |
| 241 | CACGGAAGGA GTGCTTTAGT TGTAGTTCTT GAGGTCTTCT ACGTGTACGG CATAGTCGAT |
| 301 | GCTAGGGAAA CGAACAAGAG GGGCACCAGG TGACGACTCG TCGATGTCAG CATGGAAGCC |
| 361 | AGCAGCCGCC AGGACAGGCG TCAAGGCAAC GAGTGGGAGT AAAGCTTCAA TGGCGCTGTC |
| 421 | TTTGCTGACT TTCGAGATCC AGGAGGTCTC GGCAGACTCG CTGACGGACT GGAGCAGCTC |
| 481 | CGAATTC |

The molecular weights of the primary in vitro translation products directed by mRNA specific for immunogens A, B, C and H were determined. In vitro translation of mRNA extracted from unsporulated oocysts, sporulating oocysts and sporozoites was performed using the rabbit reticulocyte cell free translation system, with either $^{35}$S-methionine or $^3$H-leucine as the incorporated indicator isotope. Specific in vitro translation products were immunoprecipitated using monospecific antibodies, prepared as described in Example 6. The protocol for in vitro translation was as described in the technical bulletin from Promega Biotec (according to manufacturer's instructions) and for immunoprecipitation as in Taylor, et al., Mol. Biochem. Parasitol. 10:305–318 (1983). The group A primary translation product recognized by monospecific antibody has a molecular weight of 24 kD. The major group B immunogen from clone SO7 has a molecular weight of 28 kD while the minor immunogens have molecular weights of 170, 24, 22, 16, and 12 kD. The additional minor specifically immunoprecipitable in vitro translation products were detectable when $^3$H-leucine was used as the labelled precursor amino acid. The 170 kD plus 22 kD minor immunogens were also detectable with $^{35}$S-methionine. The major 28 kD immunogen was detectable only when $^3$H-leucine was used as the precursor amino acid. The molecular weight for the group C immunogen was not determined. The major group H immunogen from clone SO311 has a molecular weight of 28 kD while the minor immunogens have molecular weights of 48, 38, 33, 16, 13, 12 and 10 kD. The additional minor specifically immunoprecipitable in vitro translation products were detectable when $^{35}$S-methionine was used as the labelled precursor amino acid. The major 28 kD immunogen was detectable when both $^{35}$S-methionine and $^3$H-leucine were used.

The specific mRNAs extracted from unsporulated and sporulating oocysts and/or sporozoites of E. tenella, Example 5, were sized by Northern blot analysis according to the method of Maniatis, et al. and the method described in Transfer and Immobilization of Nucleic Acids to S & S Solid supports, published by Schleicher and Schuell, Inc., pgs. 16–19 (1987). The mRNA complimentary to group A clone SO67, was 2.15±0.13 kilobases (kb), to group B, clone SO7, was 1.23±0.22 kb; to group C, clones SP54 and SP59, was 1.12±0.08 kb; and to group H, clone SO311, was 0.98±0.07 kb.

Molecular weights and isoelectric points of E. tenella immunogens were also determined. Molecular weights were determined by analytical sodium dodecyl sulphate (SDS) polyacrylamide gel electrophoresis (PAGE) of samples prepared from sporulated oocysts and/or sporozoites of E. tenella, followed by transfer to nitrocellulose and immunodetection by Western blotting as described in Example 6. Isoelectric points were determined by Western blotting of two dimensional gels of samples as described above. The dimensional gels were run according to the procedure of O'Farrell, J. Biol. Chem. 250: 4007–4021 (1975). Antibodies for both procedures were prepared as stated in Examples 2 and 6. The results are shown in the following table.

TABLE 13

Molecular Weight & Isoelectric Points of Native E. tenella Immunogens

| Immunogen group | Representative clones | Molecular weight (kD) | Isoelectric point |
|---|---|---|---|
| A | SO6, SO67 | 24 | 3.65 |
| B | SO7, SO7' | 27–28 | 5.1–6.3 |
| | | 22, 19, 18, 14, | |
| | | 12, 9, 6 | |
| C | SP54, SP59 | 21–22 | n.d. |
| H | SO311 | 28, 18 | 6.65 |
| | | 27, 24, 23, 17 | |
| | | 14, 12, 9 | |
| F | SO216 | 26–29 | n.d. |

The predominant B immunogen is characterized as a diffuse doublet of 27–28 kD on SDS-PAGE with the minor immunogens appearing as faint bands suggesting some sharing of antigenic determinants within E. tenella. The 27–28 doublet produces multiple spots on isoelectric focusing, in the range between pH 5.1 and 6.3. The pIs of the faint additional bands detected by Western blotting were not determined.

EXAMPLE 15

Induction Of Protection To Challenge With E. tenella By Recombinant-Derived E. tenella Immunogens Broiler pullets were immunized three times via the intramuscular route on days 2, 9 and 16 days of age with samples containing 10 mg of the specific recombinant fusion immunogen, from Example 13, in phosphate buffered saline absorbed on alum, 0.4% final concentration, in a total volume of 0.12 ml per dose per bird. The immunogen-alum complex was prepared by the procedure of Weir, Handbook of Experimental Immunology, Blackwell Scientific Publications London, pg. A3.11 (1978). Experimental and control birds were challenged at day 23, seven days after the final immunization, with an oral inoculation of from 5 to 30×10$^3$ sporulated oocysts, an amount sufficient to yield a mean lesion score of at least 2.5 in non-immunized controls at 30 days of age. Seven days after challenge the chickens were killed and the severity of the lesions in the ceca was determined according to the method of Johnson and Reid, Exp. Parasitol. 28:30–36 (1970). Representative examples of the results are shown in Tables 14–18.

TABLE 14

Protection Of Chickens Against Coccidiosis
With Group A Immunogen SO67-CheY

| Challenge dose (x $10^{-3}$) | Immunized infected | Non-Immunized infected |
|---|---|---|
| 5 | 2.18 | 3.41 |
| 10 | 2.57 | 3.57 |
| 15 | 1.78 | 3.44 |

TABLE 15

Protection Of Chickens Against Coccidiosis
With Group B Immunogen SO7-CheY

| Challenge dose (x $10^{-3}$) | Immunized infected | Non-Immunized infected |
|---|---|---|
| 10 | 1.41 | 3.00 |
| 20 | 1.28 | 3.43 |
| 30 | 1.34 | 3.38 |

TABLE 16

Protection Of Chickens Against Coccidiosis
With Group C Immunogen SP54-CheY

| Challenge dose (x $10^{-3}$) | Immunized infected | Non-Immunized infected |
|---|---|---|
| 5 | 1.71 | 3.38 |
| 10 | 1.68 | 3.00 |
| 15 | 1.93 | 3.22 |

TABLE 17

Protection Of Chickens Against Coccidiosis
With Group H Immunogen SO311-CheY

| Challenge dose (x $10^{-3}$) | Immunized infected | Non-Immunized infected |
|---|---|---|
| 10 | 2.03 | 2.97 |
| 15 | 2.00 | 3.32 |

TABLE 18

Protection Of Chickens Against Coccidiosis
With Group F Immunogen SO216-CheY

| Challenge dose (x $10^{-3}$) | Immunized infected | Non-Immunized infected |
|---|---|---|
| 10 | 1.50 | 2.16 |
| 15 | 1.30 | 2.72 |
| 20 | 1.25 | 2.89 |

These results show that recombinant *E. tenella* immunogens A, B, C, H, and F can be used to immunize two-day-old chickens against coccidiosis. Three intramuscular inoculations provide a high level of protection against the disease as indicated by the absence of severe lesion development in immune birds after a normally virulent infection.

EXAMPLE 16
Isolation Of The Native Form Of The B Immunogen From *E. Tenella*

A suspension of $1 \times 10^9$ sporulated oocysts of *E. tenella* in 20 ml of phosphate buffered saline (PBS) containing 0.1 mM PMSF was sonicated in an ice bath for a total of 10 minutes, in 2.5 minute bursts using a Branson Sonic Power Co. Sonifier Cell Disrupter 350 (duty cycle 30%, output control 4). The sonicate was centrifuged at 27,000×g for 30 minutes at 4° C. The pellet was washed 3 times in 40 ml PBS/0.1 mM PMSF, and was recovered by centrifugation as described above. The washed pellet was resuspended in 60 ml of 5M guanidine-HCl/0.5M Tris-HCl, pH 8.6, and 400 mg DTT. Reduction was allowed to proceed for 3 hours at 20° C. with mild agitation. Insoluble debris was removed by centrifugation as described above. The supernatant fluid, containing reduced and solubilized B antigen was concentrated by ultra-filtration (Ultrafilter PM-10, Amicon Corp.) to 20 ml, and iodoacetic acid (400 mg) was added. The pH was readjusted to 8.6 by the addition of 3M Tris base, and carboxymethylation was allowed to proceed for 60 minutes at 20° C. in the dark. The reaction mixture was then dialyzed for 48 hours against 0.05M $NH_4HCO_3$/0.1 mM PMSF/ 0.02% sodium azide. With the removal of guanidine-HCl, some insoluble material formed which was subsequently removed by centrifugation as described above. The cleaned supernatant was then concentrated to 12 ml by ultrafiltration, as described above. The concentrate was then applied to a sizing column of Sephacryl S-200 (87×2.5 cm) equilibrated in 0.05M $NH_4HCO_3$, 0.1% Zwittergent 3-12 (Calbiochem), 0.02% sodium azide. A total of 120×4.5 ml fractions were collected, at a flow rate of 25 ml/hour. Effluent fractions were monitored at 280 nm, and the elution of the B immunogen was monitored by Western blotting, initially using rabbit anti-sporozoite antiserum, and subsequently with a rabbit antiserum to the SO7/CheY protein. Fractions containing the B antigen (47–57) were pooled, concentrated to 10 ml, and were reapplied to the column. The column was eluted and monitored as before. Pooled fractions were concentrated to a volume containing approximately 0.5 mg protein/ml. The total yield was 5.8 mg.

SDS gel analysis showed a single homogeneously pure protein of 30 kD±3 kD, which on Western blot analysis was reactive with both rabbit anti-sporozoite antiserum and rabbit anti-SO7-CheY.

The immunogenic activity of this sample of B antigen purified from *E. tenella* was measured as described in Example 15. Two day old broiler pullets were immunized three times via the intramuscular route on days 2, 9 and 16 with samples containing 10 mg of the purified native B immunogen absorbed on alum (0.4% final concentration). The immunogen-alum complex was prepared by the procedure of Weir, Handbook of Experimental Immunology, Blackwell Scientific Publications, London, pg. A3-11 (1978). Experimental and control birds were challenged at day 23, seven days after the final immunization with an oral inoculation of from $5-15 \times 10^3$ sporulated oocysts. Seven days after challenge, the chickens were killed and the severity of the lesions in the ceca was determined according to the method of Johnson and Reid, Exp. Parasitol, 28, 30–36 (1970). Results are presented as mean cecal lesion scores for groups of eight birds and are shown in the following table.

TABLE 19

Protection of Chickens Against Coccidiosis
With Native Group B Immunogen

| Challenge Dose ($\times 10^{-3}$) | Immunized Infected | Non-Immunized Infected |
| --- | --- | --- |
| 5 | 1.36 | 3.41 |
| 10 | 1.64 | 3.57 |
| 15 | 1.54 | 3.44 |

TABLE 20

Protection of Chickens Against Coccidiosis
With Native Group B Immunogen

| Challenge Dose ($\times 10^{-3}$) oocysts | Immunized Infected | Non-Immunized Infected |
| --- | --- | --- |
| 10 | 1.41 | 3.00 |
| 20 | 1.44 | 3.43 |
| 30 | 1.59 | 3.38 |

An alternative method of purifying the B immunogen from E. tenella is by affinity chromatography, using the antibody to the SO7-CheY protein. For this purpose, two affinity columns were prepared, one using serum from a rabbit removed prior to immunization with the SO7-CheY antigen (prebleed column), and one using antiserum from the same rabbit immunized with the SO7-CheY antigen, using the immunization regime described in Example 2. The SO7-CheY immunogen was prepared as described in Example 13. The immunoglobulin IgG fraction was prepared from 4 ml of each serum, using the method of Corthier, et al., J. Immunol. Met., 66, 75–79 (1984). For each column, 15 mg of IgG was coupled to 0.5 gm of Sepharose-Protein A (Sigma), using the method of Schneidert, et al., J. Biol. Chem. 257, 10766–10769 (1982). Coupling efficiency was between 75–95%. For immunoaffinity purification, approximately 5 mg of the reduced, carboxymethylated extract, prepared as described above (with no purification by gel filtration), on 0.1M borate buffer, pH 8.1, 0.5M NaCl, 0.02% NaN$_3$, 0.1 mM PMSF, was applied to the prebleed column equilibrated in the same buffer. The column was washed with 3 ml of column buffer, and the combined column flow-through and washes were then applied to the anti-SO7/CheY column equilibrated in the same buffer. The column was washed with 10 ml of column buffer, prior to elution with 3M NaSCN. The eluate was dialyzed for 48 hours versus 0.05M NH$_4$HCO$_3$, prior to freezing. A total of approximately 50 mg protein was recovered in the final eluate.

The immunogenic activity of this affinity purified B antigen from E. tenella was tested as described in Example 15. Two day old broiler pullets were immunized three times via the intramuscular route on days 2, 9 and 16 with samples containing approximately 0.3 mg of the immunoaffinity purified Group B immunogen absorbed on alum (0.4% final concentration). The immunogen-alum complex was prepared by the procedure of Weir, Handbook of Experimental Immunology, Blackwell Scientific Publications, London, pg. A3-11 (1978). Experimental and control birds were challenged at day 23, seven days after the final immunization, with an oral inoculation of from 10–30×10$^3$ sporulated oocysts. Seven days after challenge, the chickens were killed, and the severity of the lesions in the ceca was determined according to the method of Johnson and Reid, Exp. Parasitol. 28, 30–36. Results are presented as mean cecal lesion scores for groups of eight birds and are shown in the following table.

EXAMPLE 17

Identification And Isolation Of B Antigens From Other Eimeria Species

E. acervulina antigens were prepared by resuspending sporulated oocysts at a concentration of 5.5×10$^7$ per ml and DEAE-52 purified sporozoites at a concentration of 2.6×10$^8$ per ml in NET buffer (10 mM Tris-HCl, pH 8.0, 150 mM NaCl, 5 mM EDTA) containing a cocktail of protease inhibitors (2 mg/ml 1-10 phenanthroline, 2 mg/ml benzamidine, 0.002 mg/ml PMSF, 0.048 mg/ml Sigma soybean trypsin inhibitor, 0.048 mg/ml aprotinin, 0.02 mg/ml leupeptin). At this point, the samples were mixed with an equal volume of 2× sample buffer (0.125M Tris-HCl, pH 6.8, 4% v/v SDS, 10% v/v 2-mercaptoethanol, 20% glycerol). The samples were boiled for 3 minutes, sonicated till fully disrupted, and reboiled again for 3 minutes. Bromophenol blue was added to 0.0025% and the samples were stored at −20° C. until ready for use.

For immunoblotting, antigens obtained from 3×10$^5$ sporulated oocysts and 2×106 sporozoites were loaded per slot and subjected to electrophoresis on a 5–20% SDS-polyacrylamide gradient gel (Laemmli, Nature 227: 680–684, 1970). Proteins separated by SDS-PAGE were electrophoretically transferred to nitrocellulose by the technique of Towbin et al, Proc. Natl. Acad. Sci. U.S.A. 76: 4350–4354 (1979). The nitrocellulose was blocked with 0.5% gelatin in phosphate buffered saline, pH 7.4, for 1 hour with three 200 ml washes followed by a second blocking with 0.25% gelatin in TEN buffer (50 mM Tris-HCl, 150 mM NaCl, 5 mM EDTA, pH 7.4) for 1 hour and washed as before. After blocking, the nitrocellulose was incubated overnight at room temperature in 20 ml of antibody (raised against the CheY fusion protein containing the E. tenella clone SO7 sequence, representing the B antigen of E. tenella) diluted 1:100 with TEN buffer containing 0.25% gelatin and 0.05% Triton X-100. The filters were washed 5 times for 20 minutes each with 200 ml of TEN containing 0.25% gelatin. Bound antibody was detected with 125I-protein A diluted in 20 ml of TEN, 0.25% gelatin, 0.05% Triton to a final concentration of 2×10$^5$ cpm/ml. Incubation with radiolabeled protein A was carried out for 1 hour at room temperature, after which time the filters were washed 2 times for 15 minutes with 200 ml of TEN containing 0.25% gelatin and 0.05% Triton and 4 times for 15 minutes with 200 ml of TEN. After washing, the filters were air dried and exposed to Kodak X-omat AR film. The antigen had a molecular weight of approximately 26 kD±3 kD.

E. maxima sporulated oocysts stored in phosphate-buffered saline (PBS) pH 7.6 were centrifuged for 10 minutes at 1600×g and were resuspended in a volume of PBS equal to the packed cell pellet. To this suspension, an equal volume of glass beads was added and the oocysts were broken by orbital shaking at 200 rpm, Dulski, P. and Turner, M., Avian Diseases 32: 235–239, 1988. The disrupted oocysts and sporocysts were collected by centrifugation at 1600×g for 10 minutes. The pellet was then resuspended in 50% Percoll/1X PBS and recentrifuged. The pellet containing clean sporocysts was collected and washed 2 times with PBS before proceeding. Undisrupted oocysts were collected from the top of the Percoll gradient, washed, and the entire procedure was repeated when necessary. Approximately 1.5 to 2 sporocysts were obtained per sporulated oocyst.

Antigens were prepared by resuspending the sporocysts at a concentration of $5\times10^7$ per ml in NET buffer containing a cocktail of protease inhibitors. At this point, the samples were mixed with an equal volume of 2× sample buffer. The samples were boiled for 3 minutes, sonicated till fully disrupted, and reboiled again for 3 minutes. Bromophenol blue was added to 0.0025% and the samples were stored at −20° C. until ready for use.

For immunoblotting, antigens obtained from $1\times10^6$ sporocysts were loaded per slot and subjected to electrophoresis on a 5–20% SDS-polyacrylamide gradient gel (Laemnmli, Nature 227: 680–684, 1970). Proteins separated by SDS-PAGE were electrophoretically transferred to nitrocellulose by the technique of Towbin et al, Proc. Natl. Acad. Sci. U.S.A. 76: 4350–4354 (1979). The nitrocellulose was blocked with 0.5% gelatin in phosphate buffered saline, pH 7.4, for 1 hour with three 200 ml washes followed by a second blocking with 0.25% gelatin in TEN buffer (50 mM Tris-HCl, 150 mM NaCl, 5 mM EDTA, pH 7.4) for 1 hour and washed as before. After blocking, the nitrocellulose was incubated overnight at room temperature in 20 ml of antibody (raised against the CheY fusion protein containing the E. tenella clone SO7 sequence, representing the B antigen of E. tenella) diluted 1:100 with TEN buffer containing 0.25% gelatin and 0.05% Triton X-100. The filters were washed 5 times for 20 minutes each with 200 ml of TEN containing 0.25% gelatin. Bound antibody was detected with $^{125}$I-protein A diluted in 20 ml of TEN, 0.25% gelatin, 0.05% Triton to a final concentration of 2×105 cpm/ml. Incubation with radiolabeled protein A was carried out for 1 hour at room temperature, after which time the filters were washed 2 times for 15 minutes with 200 ml of TEN containing 0.25% gelatin and 0.05% Triton and 4 times for 15 minutes with 200 ml of TEN. After washing, the filters were air dried and exposed to Kodak X-omat AR film. The antigen had a molecular weight of approximately 28 kD±3 kD.

Sporulated oocysts were furnished as a 20 ml suspension in PBS, containing approximately 7×19 oocysts/ml. The suspension was made with 0.1 mM in PMSF, and then sonicated in an ice-bath until by microscopic examination no more than about 10% of intact sporozoites remained. The sporulated oocyst sonicate insoluble fraction, which contains the B-antigen, was obtained by collecting the pellet following centrifugation at 30,000×g for 45 minutes at 4° C. The B-antigen was extracted from the sonicate pellet by reduction and carboxymethylation. Briefly, the pellet was washed three times in PBS, then suspended in 60 ml 5M guanidine-HCl/0.5M Tris-HCl, pH 8.6 at room temperature. The suspension was then charged with 400 mg DTT and kept at room temperature for 24 hours with mild agitation. The suspension was then centrifuged at 30,000×g for 60 minutes at 4° C., and the supernatant fluid was concentrated to 20 ml by ultrafiltration on an Amicon YM 10 membrane. The concentrate was charged with a fourfold molar excess, with respect to DTT, of 630 mg iodoacetic acid. The pH was adjusted immediately to 8.6 with 3M Tris base, and the system was kept at room temperature and in the dark for 2 hours, followed by dialysis against 50 mM NH4HCO3/0.1 mM PMSF/0.02% sodium azide for 48 hours, with several changes of the permeate. During dialysis, some insoluble matter formed which was removed by centrifugation at 30,000×g for 30 minutes at 4° C. The retentate constitutes the reduced and carboxymethylated soluble fraction (RCSF), containing on the average 400 mg protein/ml in a total of about 30 ml.

RCSF derived from E. acervulina was applied to a column (100×2 cm) of Sephacryl S-200 equilibrated in running buffer (50 mM NH4HCO3/0.1% zwittergent/0.1 mM PMSF, 0.02% sodium azide). A total of 60 fractions (5.5 ml) were collected. Fractions containing the antigen were identified by SDS-PAGE followed by Western blotting, using antiserum raised against the CheY fusion protein containing the E. tenella clone SO7 sequence, representing the B antigen of E. Tenella. Appropriate fractions were pooled and concentrated to ca. 12 ml by ultrafiltration (Amicon, YM10 membrane). The concentrate was then passed over an affinity matrix constructed with pre-bleed IgG isolated from serum of the rabbit subsequentially injected with the SO7 fusion protein. Passage was done by continuous recycling for 18 hours at 4° C. The flow-through from this step, containing the B-antigen, was diafiltered (Amicon, YM10 membrane) with 50 mM sodium bicarbonate buffer to remove the zwittergent, then with column wash (0.1M sodium borate, pH 8.0/0.5M NaCl, 0.02% sodium azide/0.1 mM PFST). Final volume was about 12 ml and this constituted the charge (14361-216-2) to the biospecific matrix containing the rabbit anti-SO7'IgG. The charge was applied to the matrix by recycling for 18 hours at 4° C.

After draining the column of the charge fluid, the matrix was washed with the following and in the order indicated:
2×5 ml column wash
2×5 ml 10 mM Tris-HCl, pH 8.0

The antigen was then desorbed from the matrix by gravity passage of 10 ml of 0.1% zwittergent 3-12 in 10 mM Tris-HCl, pH 8.0. The eluate was dialysed against 50 mM NH4HCO3 and concentrated to 5.0 ml by ultrafiltration (Amicon, YM10 membrane). The protein was characterized by SDS-PAGE and silver staining.

The purification of the B-antigen from E. maxima followed a similar protocol as described, but pre-purification on Sephacryl S-200 was omitted. RCSF from E. maxima, 20 ml, was sub-aliquoted (10 ml each). The aliquot was charged with noctyl glucoside to 0.2% and with NaCl to 0.5M and was then passed by recycling over a pre-bleed column for 18 hours at 4° C. The flow-through from this step constituted the column charge to the biospecific matrix, constructed with anti-SO7 IgG. Washing of the matrix and desorption of the antigen therefrom, was done as described above. The eluate was diafiltered with 10 mM Tris-HCl, pH 8.0 (Amicon YM10 membrane) to remove zwittergent, and was reconstituted in 2.5 ml 4M urea (final product 38893-49-3). The product was characterized by SDS-PAGE and silver staining.

Biospecific matrices were prepared based on the method of Bethel, et al., see above. This 1,1-carbonyldiimidazole activated support is available commercially under the trade name Reactigel (Pierce Chem. Co., Rockford, Ill.), the feature of this support rests in the formation of a very stable and uncharged N-alkyl carbamate bond on reaction with a free amino group on the ligand. Reactigel was used in accordance with the manufacturer's suggested procedure. Briefly, 5 cc of an acetone suspension (50% bed volume) of Reactigel was transferred into an Econocolumn (BioRad) and drained free of acetone. IgG was then introduced as a solution of 12 mg/8 ml coupling buffer (0.1M NaHCO$_3$/

0.5M NaCl, pH 8.5). The column was sealed, mounted on a rocking platform and kept at 4° C. overnight. The column was drained, and washed with 5 ml coupling buffer. Quenching was done by suspending the support in 10 ml coupling buffer containing 50 ml aminoethanol and placing the column on a rocking platform for 4 hours at room temperature. he matrix was then washed with 10 ml coupling buffer, 6 ml 3.5M sodium thiocyanate, and finally with 10 ml "column wash" (0.1M borate buffer, pH 8.0, 0.5M NaCl, 0.02% sodium azide, 0.1 mM PMSF).

Chickens were immunized with the Group B immunogen isolated from *E. acervulina* and challenged with sporulated oocysts. The results are shown in the following table.

TABLE 21

Protection of Chickens Against Coccidiosis With Native Group B Immunogen From *E. acervulina*

| | Mean Lesion Score Challenge Organism | | | |
|---|---|---|---|---|
| | *E. acervulina** | | *E. tenella** | |
| Antigen | Trial 1 | Trial 2 | Trial 1 | Trial 2 |
| None | 2.90 | 2.40 | 2.75 | 2.46 |
| *E. tenella* Recombinant Group B | 1.64 | 1.65 | 2.13 | 1.60 |
| *E. acervulina* Group B 0.1 mg | 2.17 | 1.90 | 1.61 | 1.32 |
| *E. acervulina* Group B 0.3 mg | 1.90 | 1.15 | 2.03 | 1.36 |

*Challenge doses: *E. acervulina* 1–2 × $10^5$, *E. tenella* 2–5 × $10^4$

Samples of the expression vector pJC264 containing the DNA for the various *E. tenella* immunogens have been deposited in a host *Escherichia coli,* JM83 or JM109, under the Budapest Treaty in the American Type Culture Collection, 12301 Parklawn Drive, Rockville, Md. 20852, U.S.A. On Nov. 4, 1987, samples of the expression vector containing clones SO7, SO6, SP54 and SO311 were deposited and were given accession numbers 67577, 67559, 67556 and 67558 respectively. On Dec. 19, 1987, a sample of the expression vector containing clone SP59 was deposited and given accession number 67594. On Jan. 8, 1988, a sample of expression vector containing clone SO216 was deposited and given accession number ATCC 67600.

What is claimed is:

1. A recombinant DNA molecule having a nucleotide sequence encoding an amino acid sequence of the Group B immunogen SO7 depicted in Table 8.

2. The recombinant DNA molecule of claim 1 wherein the nucleotide sequence is the nucleotide sequence of clone SO7 depicted in Table 8.

3. An immunogenic composition comprising the DNA of claim 1.

4. A method of immunizing poultry against *E. tenella* induced coccidiosis comprising administering an therapeutically effective dose of the composition of claim 3.

* * * * *